US012595454B2

(12) United States Patent
Yin et al.

(10) Patent No.: US 12,595,454 B2
(45) Date of Patent: Apr. 7, 2026

(54) METHODS OF CONTINUOUS CELL CULTURE

(71) Applicant: Momenta Pharmaceuticals, Inc., Titusville, NJ (US)

(72) Inventors: Jin Yin, Sudbury, MA (US); Ru Zang, Auburndale, MA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 1068 days.

(21) Appl. No.: 17/273,004

(22) PCT Filed: Aug. 28, 2019

(86) PCT No.: PCT/US2019/048594
§ 371 (c)(1),
(2) Date: Mar. 3, 2021

(87) PCT Pub. No.: WO2020/051042
PCT Pub. Date: Mar. 12, 2020

(65) Prior Publication Data
US 2021/0222109 A1        Jul. 22, 2021

Related U.S. Application Data

(60) Provisional application No. 62/727,976, filed on Sep. 6, 2018.

(51) Int. Cl.
| | |
|---|---|
| *C12M 1/00* | (2006.01) |
| *C07K 16/24* | (2006.01) |
| *C12M 1/06* | (2006.01) |
| *C12M 1/34* | (2006.01) |
| *C12M 1/42* | (2006.01) |

(52) U.S. Cl.
CPC ........... *C12M 29/20* (2013.01); *C07K 16/244* (2013.01); *C12M 27/02* (2013.01); *C12M 29/06* (2013.01); *C12M 29/10* (2013.01); *C12M 35/04* (2013.01); *C12M 41/34* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 4,868,116 A | 9/1989 | Morgan et al. | |
| 4,980,286 A | 12/1990 | Morgan et al. | |
| 5,013,556 A | 5/1991 | Woodle et al. | |
| 5,308,341 A | 5/1994 | Chanoch | |
| 5,641,640 A | 6/1997 | Hanning | |
| 5,807,715 A | 9/1998 | Morrison et al. | |
| 6,146,361 A | 11/2000 | DiBiasi et al. | |
| 6,192,891 B1 | 2/2001 | Gravel et al. | |
| 6,200,296 B1 | 3/2001 | Dibiasi et al. | |
| 6,277,099 B1 | 8/2001 | Strowe et al. | |
| 6,302,855 B1 | 10/2001 | Lav et al. | |
| 7,556,615 B2 | 7/2009 | Pettis et al. | |
| 11,719,704 B2 | 8/2023 | Robblee | |
| 12,304,950 B2 | 5/2025 | Zang | |
| 12,360,119 B2 | 7/2025 | Robblee | |
| 2011/0045581 A1 | 2/2011 | Collao Olivares et al. | |
| 2013/0123126 A1 | 5/2013 | Collins et al. | |
| 2014/0271622 A1 | 9/2014 | Prentice | |
| 2014/0359902 A1 | 12/2014 | Ariaans et al. | |
| 2015/0158907 A1* | 6/2015 | Zhou | C12M 47/12 |
| | | | 530/399 |
| 2015/0204884 A1 | 7/2015 | Robblee et al. | |
| 2015/0252108 A1 | 9/2015 | Washburn et al. | |
| 2016/0032232 A1 | 2/2016 | Khan | |
| 2016/0289628 A1 | 10/2016 | Cizek et al. | |
| 2019/0025325 A1 | 1/2019 | Robblee | |
| 2020/0199525 A1 | 6/2020 | Boon et al. | |
| 2020/0399585 A1 | 12/2020 | Takahashi et al. | |
| 2021/0222109 A1 | 7/2021 | Yin et al. | |
| 2022/0033487 A1 | 2/2022 | Zang | |
| 2022/0081479 A1 | 3/2022 | Zang | |

(Continued)

FOREIGN PATENT DOCUMENTS

| | | |
|---|---|---|
| CN | 105378086 A | 3/2016 |
| CN | 105779394 A | 7/2016 |
| CN | 106029871 A | 10/2016 |

(Continued)

OTHER PUBLICATIONS

Ying Zhu et al. "NS0 Cell Damage by High Gas Velocity Sparging in Protein-Free and Cholesterol-Free Cultures". Biotechnology and Bioengineering. 2008, vol. 101, No. 4, pp. 751-760.*
Matanguihan et al. In: Animal cell Technology: from target to market. 2001, pp. 399-400.*
Alfthan et al., "Properties of a Single-Chain Antibody Containing Different Linker Peptides" Protein Eng. (1995) vol. 8, Issue 7, pp. 725-731.
Corrected Notice of Allowability for U.S. Appl. No. 16/067,411 dated Jun. 14, 2023.
European Search Report for European Patent Application No. 16882558.6 dated Jul. 8, 2019.

(Continued)

*Primary Examiner* — Vera Afremova
(74) *Attorney, Agent, or Firm* — Troutman Pepper Locke LLP

(57) ABSTRACT

The present disclosure provides, among other things, continuous culture methods for producing a cell product, e.g., a recombinant protein, e.g., a glycoprotein, e.g., an antibody agent or a fusion protein. In some instances, methods herein allow large-scale production of a recombinant protein using continuous culture methods. The present disclosure identifies and addresses a problem with current continuous cell culture techniques in that at large-scale culture of certain cells have insufficient viable cell concentrations and impaired cell viability. The present disclosure provides, in part, methods and systems for large-scale continuous culture of shear-sensitive cells.

19 Claims, 13 Drawing Sheets
Specification includes a Sequence Listing.

(56) References Cited

U.S. PATENT DOCUMENTS

2023/0324406 A1    10/2023   Robblee

FOREIGN PATENT DOCUMENTS

| CN | 107109455 A | 8/2017 |
|---|---|---|
| WO | 198902468 A1 | 3/1989 |
| WO | 198907136 A2 | 8/1989 |
| WO | WO-91/011508 A1 | 8/1991 |
| WO | 199207573 A1 | 5/1992 |
| WO | 1200230954 A1 | 4/2002 |
| WO | 2004060407 A1 | 7/2004 |
| WO | 2008128216 A1 | 10/2008 |
| WO | 2008128218 A1 | 10/2008 |
| WO | 2008128219 A1 | 10/2008 |
| WO | 2008128220 A1 | 10/2008 |
| WO | 2008128221 A1 | 10/2008 |
| WO | 2008128222 A1 | 10/2008 |
| WO | 2008128225 A1 | 10/2008 |
| WO | 2008128227 A1 | 10/2008 |
| WO | 2008128228 A1 | 10/2008 |
| WO | 2008128230 A1 | 10/2008 |
| WO | 2008130924 A1 | 10/2008 |
| WO | 2008130926 A2 | 10/2008 |
| WO | 2010071817 A2 | 6/2010 |
| WO | 2010071824 A2 | 6/2010 |
| WO | 2010085251 A1 | 7/2010 |
| WO | 2010089151 A1 | 8/2010 |
| WO | 2011069056 A2 | 6/2011 |
| WO | 2011127322 A1 | 10/2011 |
| WO | 2013181575 A2 | 12/2013 |
| WO | 2013181586 A2 | 12/2013 |
| WO | 2014193973 A2 | 12/2014 |
| WO | 2015105926 A1 | 7/2015 |
| WO | 2016128361 A1 | 8/2016 |
| WO | 2017021493 A1 | 2/2017 |
| WO | 2017117218 A1 | 7/2017 |
| WO | 2017194605 A1 | 11/2017 |
| WO | 2017207822 A1 | 12/2017 |
| WO | 2018024770 A1 | 2/2018 |
| WO | WO-2020/051042 A1 | 3/2020 |
| WO | 2020142275 A1 | 7/2020 |

OTHER PUBLICATIONS

European Search Report for European Patent Application No. 19857341.2 dated Jun. 7, 2022.
European Search Report for European Patent Application No. 19907232.3 dated Aug. 18, 2022.
Fan et al., "A Multi-Pronged Investigation into the Effect of Glucose Starvation and Culture Duration on Fed-Batch CHO Cell Culture," Biotech. & Bioeng. (2015) vol. 108, No. 10, pp. 2172-2184.
Final Office Action for U.S. Appl. No. 16/067,411 dated Oct. 7, 2022.
Fournier et al., "A Review of Glycan Analysis Requirements," BioPharm International (Oct. 1, 2015) vol. 28(10), pp. 1-10.
Gilmar et al., "Rapid Assessment of Molecular Similarity between a Candidate Biosimilar and an Innovator Monoclonal Anitbody Using Complementary LC-MS Methods," BioPharm International (Aug. 2, 2010) vol. 2010(1), pp. 1-5.
Hallewell et al., "Genetically Engineered Polymers of Human CuZn Superoxide Dismutase," J. Biol. Chem. (1989) vol. 264, No. 9, pp. 5260-5268.
McCracken et al., "Control of Galactosylated Glycoforms Distribution in the Cell Culture System," Biotechnology Progress (2014) vol. 30, No. 3, pp. 547-553.
Notice of Allowance for U.S. Appl. No. 16/067,411 dated Mar. 8, 2023.
Pacis et al., "Effects of Cell Culture Conditions on Anitbody N-Linked Glycosylation—What Affects High Mannose 5 Glycoform," Biotech. & Bioeng. (2011) vol. 108, No. 10, pp. 2348-2358.
Restelli et al., "The Effect of Cell Culture Parameters on Protein Glycosylation," Cell Engineering (Jan. 1, 2002) vol. 3, pp. 61-92.

Zhang et al., "Glycan Analysis of Therapeutic Glycoproteins," mAbs (Nov. 24, 2015) vol. 8, No. 2, pp. 205-215.
Chao et al., "Research of Therapeutic Antibody Glycosylation and Its Applications," Shandong Chemical Industry (2013) vol. 42(10), pp. 54-57, 61.
European Search Report for European Patent Application No. 232018010 dated Feb. 16, 2024.
Loebrich et al., "Comprehensive manipulation of glycosylation profiles across development scales," MABS (2019) vol. 11(2), pp. 335-349.
Non-final Office Action mailed Sep. 10, 2024 received in U.S. Appl. No. 17/419,480.
Amano et al., "Mammalian cell culture tank design by computational fluid dynamics," Hitachi Review (2007) vol. 89(5), pp. 34-37.
Non-final Office Action mailed Apr. 24, 2024 received in U.S. Appl. No. 17/273,004.
Notice of Allowance for U.S. Appl. No. 17/419,480 dated Jan. 21, 2025.
Notice of Allowance for U.S. Appl. No. 18/331,803 dated Mar. 12, 2025.
Wu, "Influence of Hydrodynamic Shear Stress on Microcarrier-Attached Cell Growth: Cell Line Dependency and Surfactant Protection" Bioprocess Engineering (1999) vol. 21, pp. 201-206.
Gooch, Keith J. and Frangos, John A., Shear sensitivity in animal cell culture, Current Opinion in Biotechnology, 4:193-196 (1993).
International Search Report for PCT/US2019/048594 (Methods of Continuous Cell Culture, filed Aug. 28, 2019), received from ISA/US, 5 pages (Nov. 15, 2019).
Written Opinion for PCT/US2019/048594 (Methods of Continuous Cell Culture, filed Aug. 28, 2019), received from ISA/US, 9 pages (Nov. 15, 2019).
Zhu, Y. et al., NSO Cell Damage by High Gas Velocity Sparging in Protein-Free and Cholesterol-Free Cultures, Biotechnology and Bioengineering, 101(4):751-760 (2008).
European Medicines Agency Evaluation of Medicines for Human Use "Assment Report for Stelara", Retrieved from the Internet:// www.ema.europa.eu/documents/assessment-report/stelara-epar-public-assessment-report_en.pdf, retrieved on Jun. 24, 2019.
Ghaderi, et al., Production platforms for biotherapeutic glycoprotins. Occurence, inpact, and challenges of non-human sialylation, Biotechnol Genet Eng Rev., (2012) 28:147-75.
Sanchez-De Melo, et al., N-glycosylation profile analysis of Trastuzumab biosimilar candidates by Normal Phase Liquid Chromatography and MALD-TOF MS approaches, J Proteomics, (2015) 12(ptB):225-33.
International Search Report for PCT/US2016/068871 issued by ISA/US, 9 gages Apr. 13, 2017.
Written opinion for PCT/US2016/068871, issued by ISA/US, 9 pages Apr. 13, 2017.
Rudikoff et al., "Single Amino Acid Substitution Altering Antigen-Binding Specificity", Proc Natl Acad Sci USA (1982) 79 (6): 1979-83.
Janeway et al., "Immuno Biology the Immune System in Hearlth and Disease", Immunobiology, 3rd edition, (1997) Publishing Inc., pp. 3:1-3:11.
Edwards et al., "The Remarkable Flexibiltiy of the Human Antibody Repertoire; Isolation of Over One Thousand Different Antibodies to a Single Protein, BLyS", J Mol Biol (2003) 14; 334(1): pp. 103-118.
Lloyd et al., "Modelling the human immune response: performance of 10" Human antibody repertoire against a broad panel of therapeutically relevant antigens", Protein Eng Des Sel (2009) 22(3): pp. 159-168, doi: 10.1093/protein/gzn058.epub Oct. 2, 20089.
Goel et al., "Plasticity within the Antigen-Combining Site May Manifest as Molecular mimicry in the Humoral Immune Response" J Immunol (2004) 173(12):7358-67.
Kanyavuz et al., "Breaking the law: unconventional strategies for antibody diversification" Nat Rev Immunol (2019) 19 6):355-368. doi:10.1038/S41577-019-0126-7.
D'Angelo et al., "Many Routes to an Antibody Heavy-Chain CDR3: Necessary, Yet Insufficient, for Specific Binding", Front Immunol. (2018) 8;9:395. doi:103389/fimmu.2018.00395.eCollection 2018.
Non-final Office Action mailed Apr. 12, 2022 received in U.S. Appl. No. 16/067,411.

(56) References Cited

OTHER PUBLICATIONS

Hamm et al, Characterizatin of N-Linked Blycosylation in a Mnoclonal Antibody Producted in NS0 Cells Using Capillary Electrophonesis with Laser-Induced Fluroescence Detection, Pharmaceuticals, (2013) 6:393-406.

Haselberg et al., "Heterogeneity assessment of antibody-derived therapeutics at the intact and middle-up level by lo-flow sheathless capillary electrophoresis-mass spectrometry", Analytica Chimica Acta (2018), 1044:181-190.

International Search Report for PCT/US2019/067916 issued by ISA/US, Apr. 14, 2020.

Written opinion for PCT/US2019/067916, issued by ISA/US, Apr. 14, 2020.

Liu, "Antibody Glycosylation and Its Impact on the Pharmacokinetics and Parmacodynamics of Monoclonal Antibodies and Fc-Fusion Proteins", Journal of pharmaceutical Sciences (2015) 104:1866-1844.

Liu et al., "Pharmacokinetics of monoclonal antibodies and Fc-fusion proteins" (2018) 9(1):15-32.

Mimura, et al., "Glycosylation engineering of therapeutic IgG antibodies: challenges for the safety, funtionality and efficacy", Protein Cell (2018) (1):47-62.

Zhang et al., "Challenges of glycosylation analysis and control: an integrated apporach to producing potimal and consistant therapeutic drugs", Drug Discovery Today (2016) 21(5)P740-765.

Hincal, "An Introduction to Safety Issues in Biosimilars/Follow-On Biopharmaceuticals", J. Med. CBR Def. (2009) 7:1-18.

Nowicki, "Basic Facts about Biosimilars", Kidney Blood Press (2007) 30:267-272.

Anumula, "Advances in fluorescence derivatization methods for high-performance liquid chromatographic analysis of glycoprotein carbohydrates" Anal. Biochem., (2006) 350(1):1-23.

Goetze et al., "High-mannose glycans on the Fc region of therapeutic IgG antibodies increase serum clearance in humans", Glycobiol (2011) 21:949-959.

Xie et al., "Rapid comparison of a candidate biosimilar to an innovator monoclonal antibody with advanced liquid chormatography and mass spectrometry technologies" (2010) mAbs, 2:379-394.

Chen, "Analysis of N-glycan from recominant immunoglobulin G by on-line reversed-phase high-performance liquid chromatography/mass spectrometry", Anal. Biochem., (2007) 370:147-161.

Forrer et al., "Chip-based gel electrophoreses method for the quantification of hallf-antibody species in lgG4 and their by- and degradation products", Anal. Biochem., (2004) 334:81-88.

Hokke et al., "Sialylated carbohydrate chains of recombinant human glycoproteins expressed in Chiese hamster ovary cells contain traces of N-glycolylneuraminic acid" FEBS Lett., (1990) 275:9-14.

Sekhon et al., "Biosimilars: an overview" Biosimilars, (2011) 1:1-11.

Schellekens et al., "Clinical comparability and European biosimilar regulations", Nat Biotechnol.. (2010) 28:28-31.

Ahn et al., "Separation of 2-aminobenzamide labeled glycans using hydrophilic interaction chromatography cols. packed with 1.7 ?m sorbent" Chrom. B, (2010) 878:403-408.

Hara et al., "Determination of Mono-O-acetylated N-Acetylneuraminic", Anal Biochem., (1989) 179:162-166.

Bitter et al., "Expression and Secretion Vectors for Yeast" Methods in Enzymol. (1987) 153:516-544.

Chen et al., "Gas-phase oligosaccharide nonreducing end (GONE) sequencing and structural analysis by reversed phase hplc/mass spectrometry with polarity switching" J. Am. Soc. Mass Spectrom., (2009) 20:1821-1833.

Dick et al. "C-terminal lysine variants in fully human monoclonal antibodies: Investigation of test methods and possible causes", Biotechnology and Bioengineering (2008) 100:1132-1143.

Roger, "Biosimilars: current status and future directions", Expert Opin. Bio. Ther., (2010) 10(7):1011-1018.

Logan et al., "Adenovirus tripartite leader sequence enhances translation of mRNAs late after infection", Proc. Natl. Acad. Sci. USA (1984) 8 1:3655-3659.

Shang et al., "Development and Application of a Robust N-Glycan Profiling Method for Heightened Characterization of Monoclonal Antibodies and Related Glycoproteins" J. Pharm. Sciences, (2014) 103:1967-1978.

Gray et al., "CO2 in Large-Scale and High-Density CHO Cell Perfusion Culture," Cytotechnology (1996) vol. 22, pp. 65-78.

* cited by examiner

Production Bioreactor    Cell Retention Device

FIG. 5
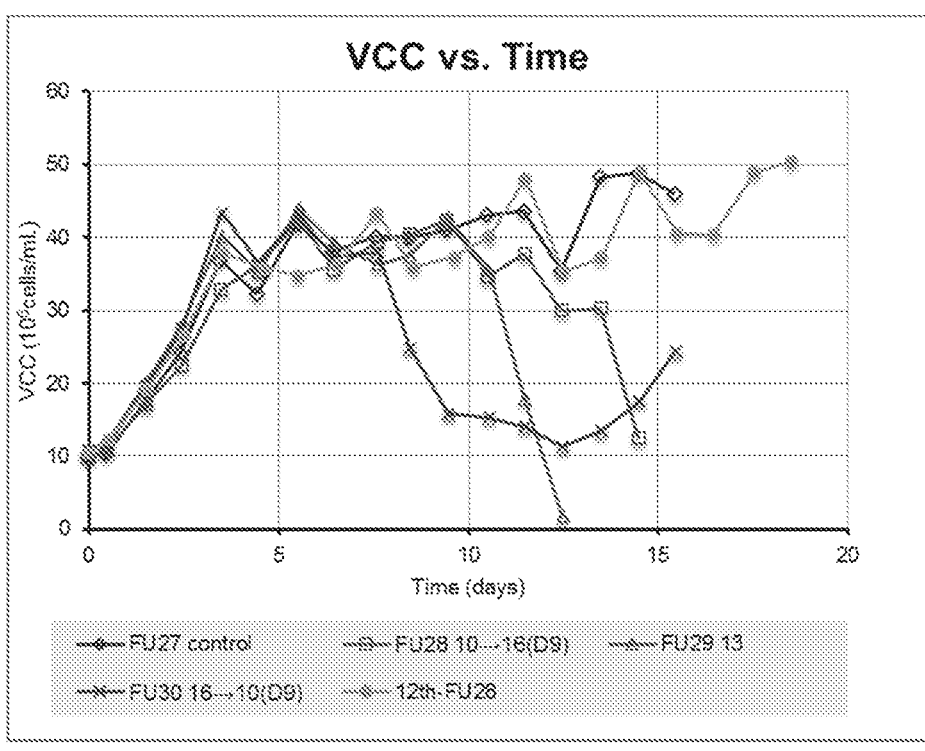
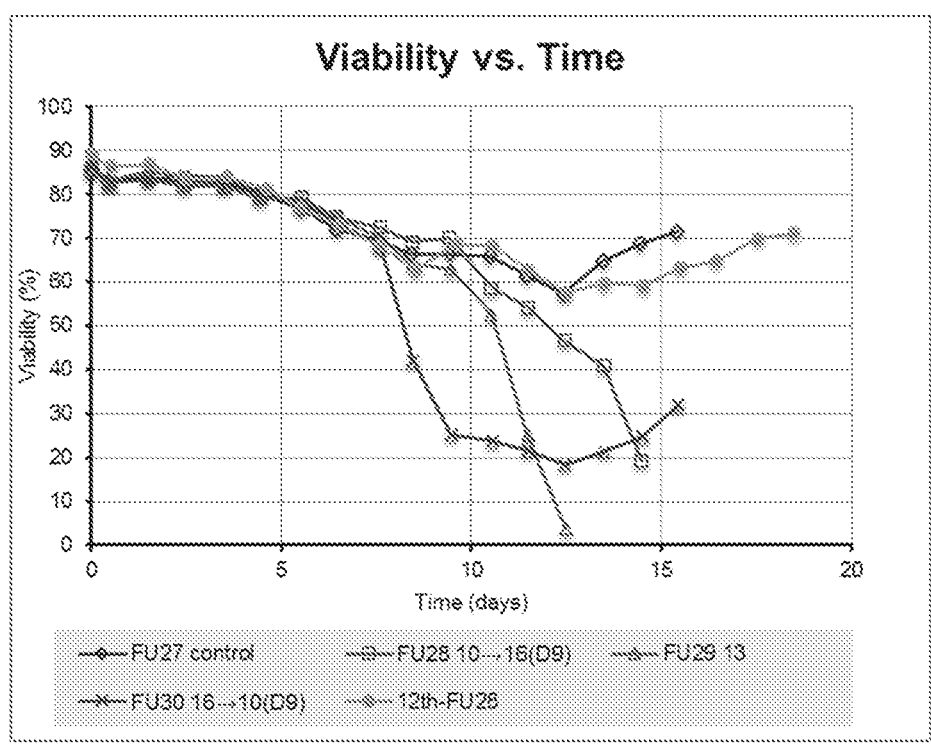

FIG. 6
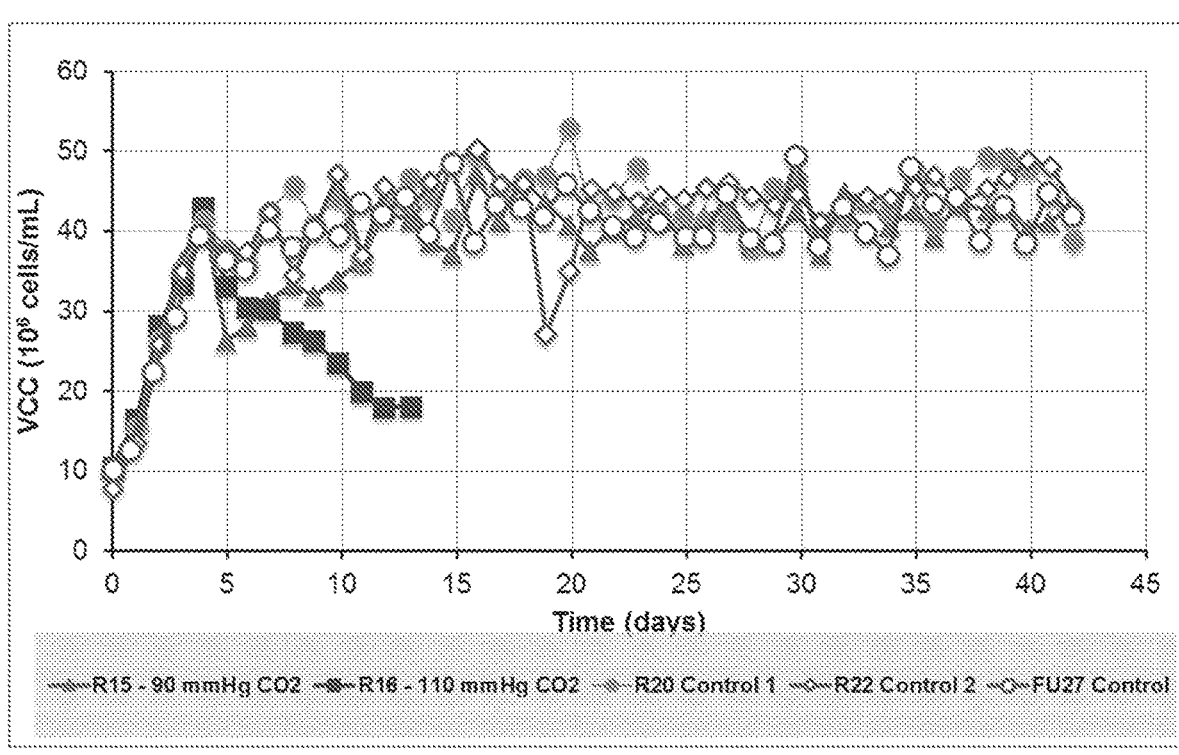
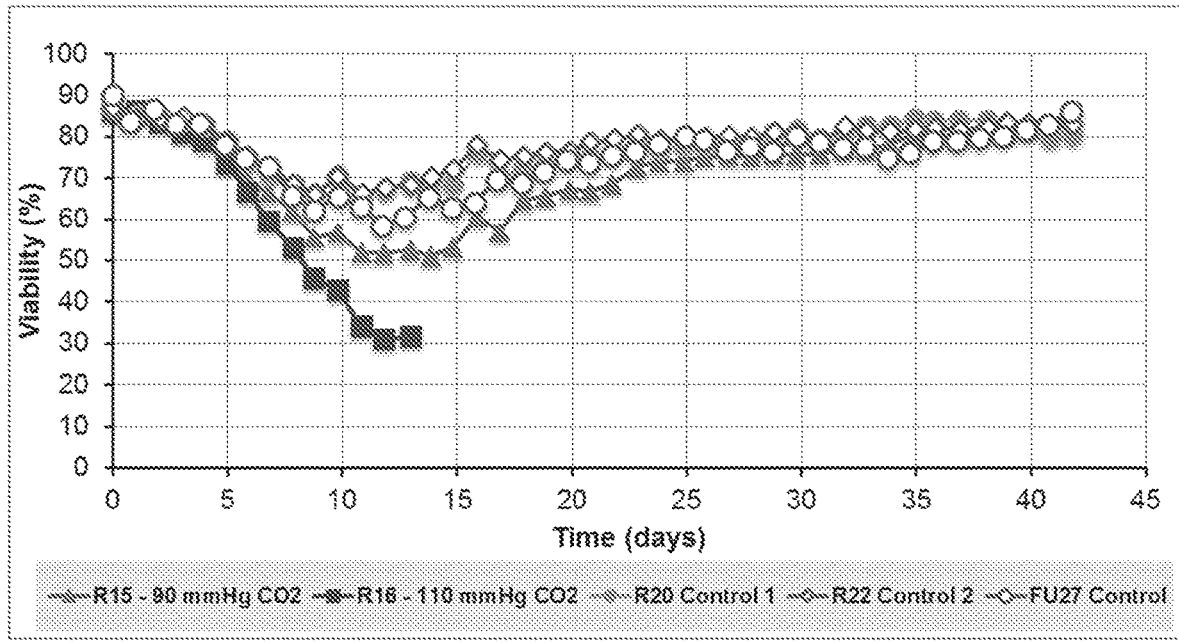

FIG. 7A
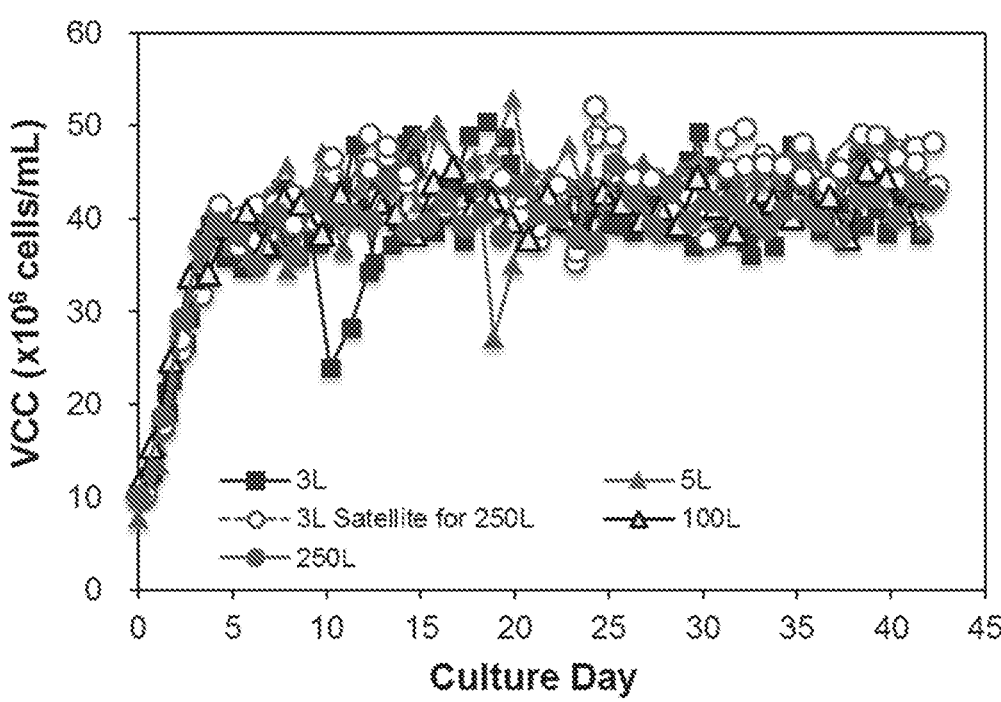
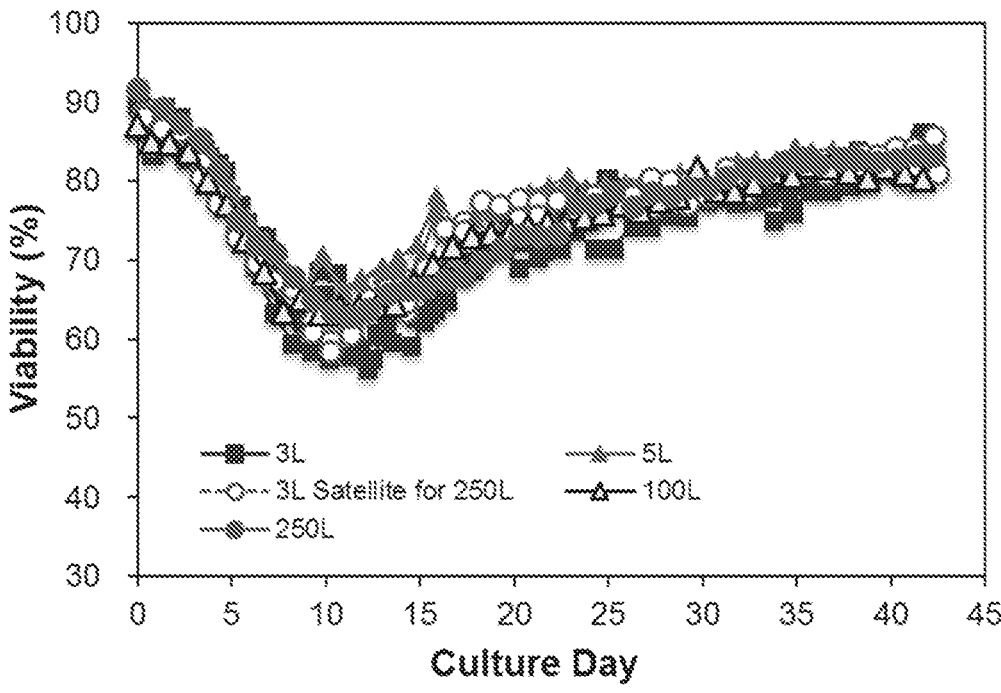

FIG. 7B
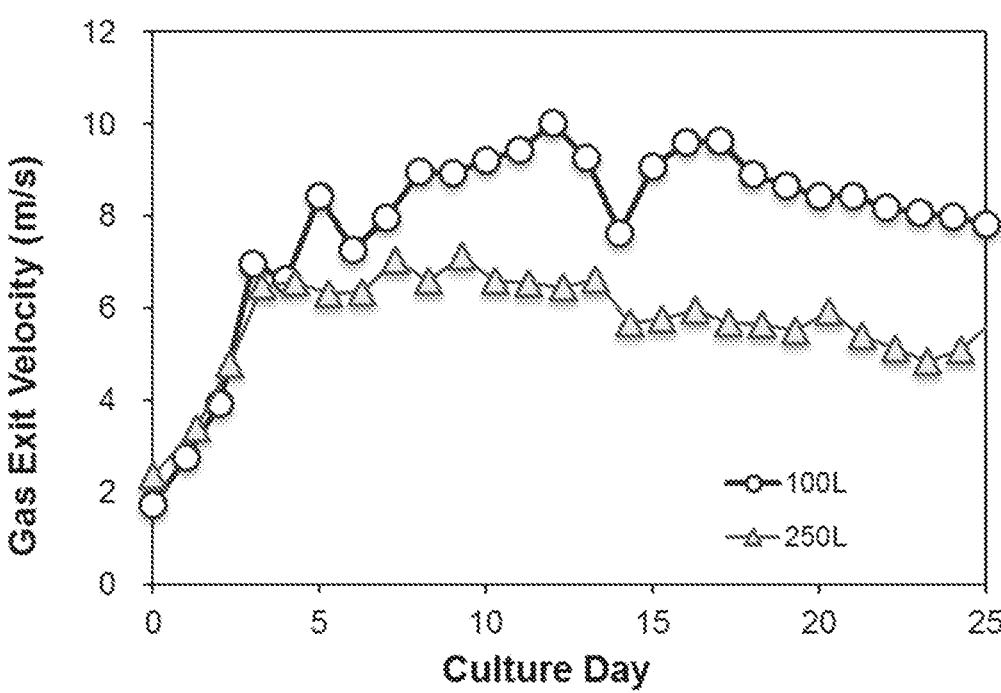
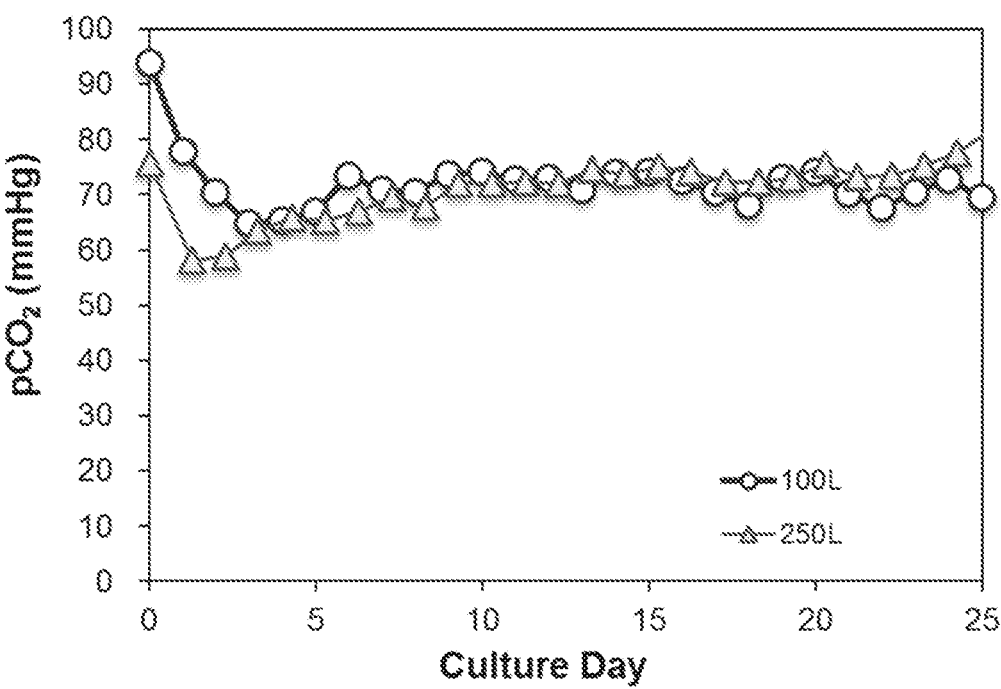

FIG. 8

| Parameter | Study Design | |
|---|---|---|
| pCO$_2$ (mmHg) | Single factor | 70 80 90 · 110 120 |
| Gas exit velocity (m/s) | Single factor | 7 8 10 · 13 16 |
| Volumetric power input (P/V: W/m$^3$) | Single factor | 30 · 200 300 |

Proven Acceptable Range (PAR)  ▽ Suboptimal  ▼ Failure Point

| Parameter | Unit | PAR & Prediction | | | Equations* |
|---|---|---|---|---|---|
| Agitation | RPM | 125 | | | |
| Volumetric power input | W/m$^3$ | 36.4 | | | $P/V \propto N^3$ |
| EDR ($\varepsilon_{ave}$) | W/m$^3$ | 30.4 | 202 | 300 | $\varepsilon_{ave} = \dfrac{N_p N^3 D^5}{V}$ |
| EDR ($\varepsilon_{max}$) | W/m$^3$ | 3270 | 6170 | 9160 | $\varepsilon_{max} = \dfrac{N_p N^3 D^5}{V_{imp}}$ |
| Max. Shear Stress | Pa | 0.8 | 2.2 | 2.8 | $\tau = \gamma\mu$ |
| $\lambda_{ave}$ | µm | 66.8 | 37.8 34.3 | | $\lambda = \left(\dfrac{\nu^3}{\varepsilon}\right)^{1/4}$ |
| $\lambda_{min}$ | µm | 18.8 | 16.1 14.8 | | |

Proven Acceptable Range (PAR)  ▼ Predicted value  ▽ Failure Point $N$:  Impeller agitation rate $\varepsilon$:  Energy dissipation rate $\tau$:  Shear stress $\lambda$:  Eddy length FIG. 9
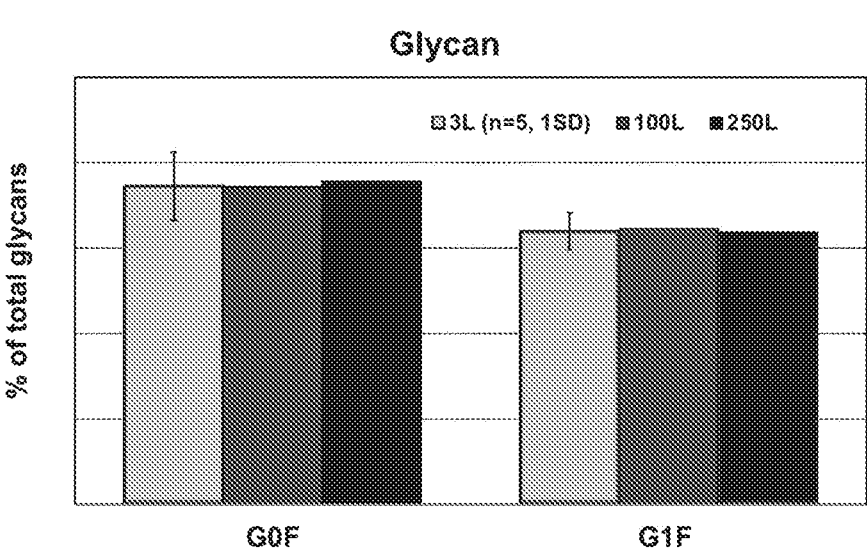
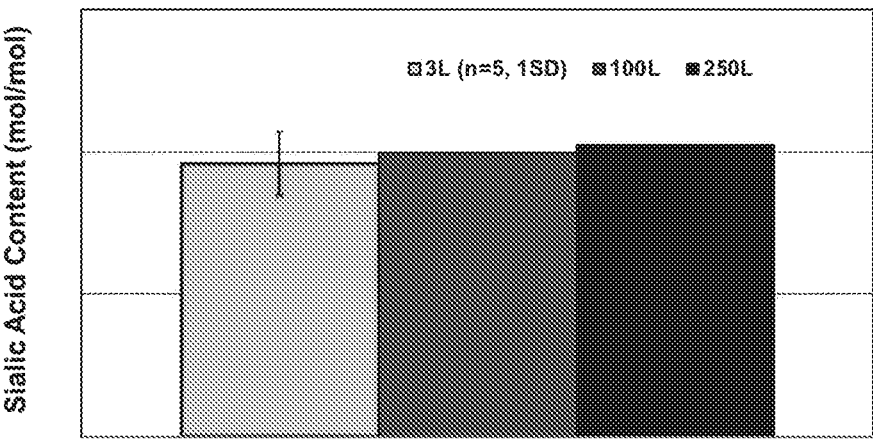

FIG. 11

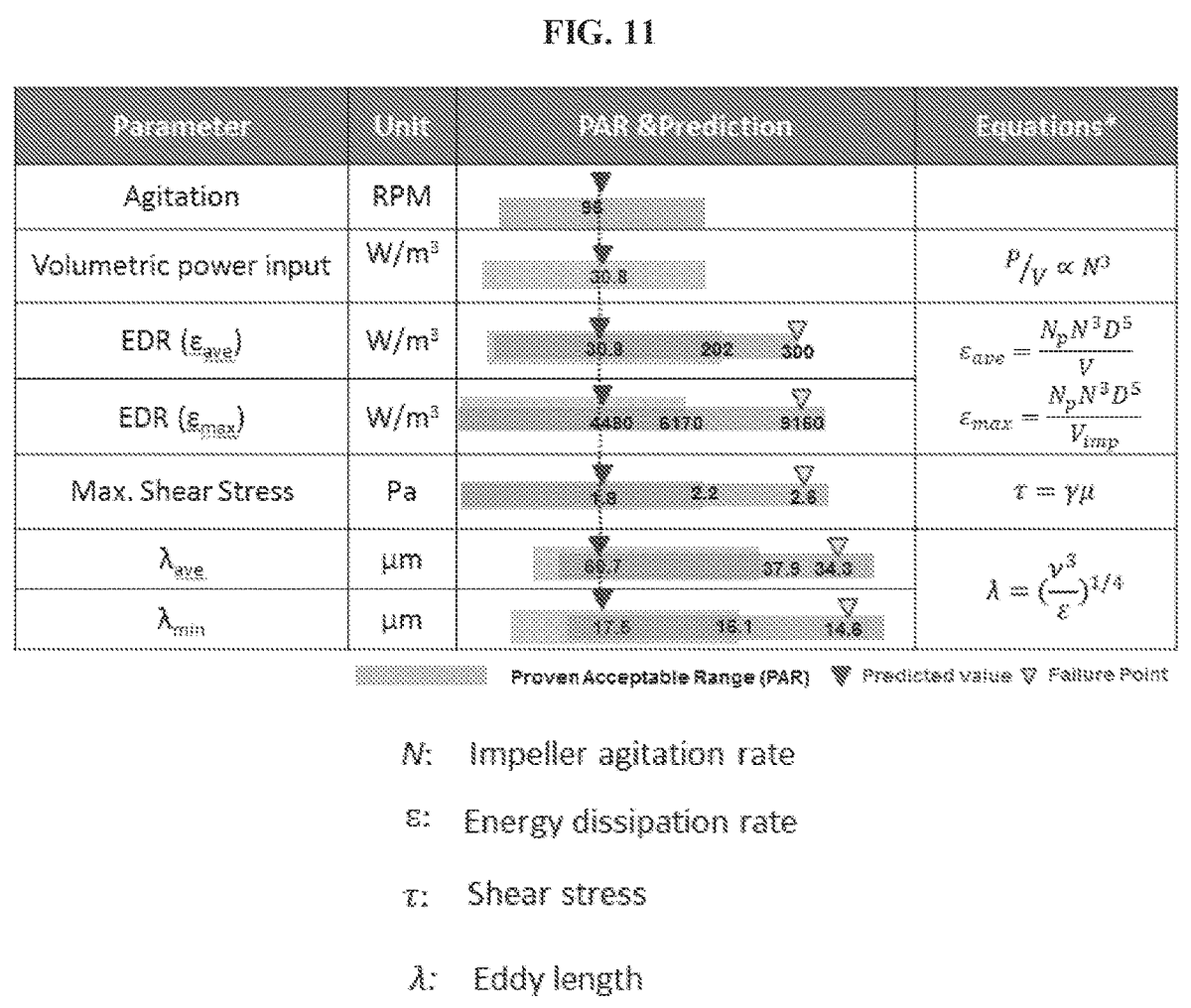

| Parameter | Unit | PAR & Prediction | Equations* |
|---|---|---|---|
| Agitation | RPM | 55 | |
| Volumetric power input | W/m³ | 32.8 | $P/_V \propto N^3$ |
| EDR ($\varepsilon_{ave}$) | W/m³ | 98.8   202   300 | $\varepsilon_{ave} = \dfrac{N_p N^3 D^5}{V}$ |
| EDR ($\varepsilon_{max}$) | W/m³ | 4480   6170   9160 | $\varepsilon_{max} = \dfrac{N_p N^3 D^5}{V_{imp}}$ |
| Max. Shear Stress | Pa | 1.8   2.2   2.8 | $\tau = \gamma\mu$ |
| $\lambda_{ave}$ | μm | 36.1   27.9   24.5 | |
| $\lambda_{min}$ | μm | 17.6   15.1   14.0 | $\lambda = \left(\dfrac{v^3}{\varepsilon}\right)^{1/4}$ |

▽ Proven Acceptable Range (PAR)   ▼ Predicted value   ▽ Failure Point

N:   Impeller agitation rate

ε:   Energy dissipation rate

τ:   Shear stress

λ:   Eddy length

FIG. 12

$$Gas\ exit\ velocity = \frac{Gas\ Flow\ Rate}{n \cdot \left(\frac{\pi d^2}{4}\right)}$$

Gas exit velocity: m/s

Gas Flow Rate: standard liter per minute (SLPM)

n: numbers of holes of the sparger d: diameter of sparger holes

METHODS OF CONTINUOUS CELL CULTURE

CROSS REFERENCE TO RELATED APPLICATIONS

This application is a national stage application under 35 U.S.C. § 371 of PCT Application No. PCT/US2019/048594, filed Aug. 28, 2019, which claims the benefit of U.S. Provisional Application No. 62/727,976, filed Sep. 6, 2018, which is hereby incorporated by reference in its entirety.

SEQUENCE STATEMENT

This application contains a computer readable Sequence Listing, which has been submitted electronically as an ASCII plain text file and is hereby incorporated by reference in its entirety. Said ASCII Sequence Listing, created on Aug. 28, 2019, is named SequenceLising_ST25.txt and is 6038 bytes in size.

BACKGROUND

Continuous cell culture methods and systems are gaining popularity in biomanufacturing. However, continuous cell culture methods and systems are associated with a number of caveats and complications. Thus, there remains a need for improved continuous cell culture methods and systems.

SUMMARY OF THE INVENTION

The present disclosure provides, among other things, continuous culture methods for producing (e.g., manufacturing) a cell product, e.g., a recombinant protein, e.g., a glycoprotein, e.g., an antibody agent or a fusion protein. In some instances, methods herein allow large-scale production of a recombinant protein using continuous culture methods (e.g., perfusion culture methods). The present disclosure identifies and addresses a problem with current continuous cell culture techniques (e.g., perfusion cell culture) in that at large-scale culture (e.g., at least 25 L, e.g., at least 100 L) of certain cells have insufficient viable cell concentrations and impaired cell viability. The present disclosure provides, in part, methods and systems for large-scale (e.g., at least 25 L, e.g., at least 100 L) continuous culture of shear-sensitive cells.

The present disclosure provides the insight that large-scale culture of shear-sensitive cells can be accomplished by controlling gas exit velocity of the bioreactor system. For example, large-scale culture of shear-sensitive cells in a bioreactor system (e.g., a perfusion bioreactor system) with a gas exit velocity that is controlled and/or maintained within a defined amount and/or range, e.g., such that it is at most 20 m/s can yield a steady state viable cell concentration of shear-sensitive cells within a range of about $20\times10^6$ cells/mL to about 15×107 cells/mL.

In some instances, provided are methods including culturing a population of cells comprising or consisting of shear-sensitive cells in a bioreactor system (e.g., a perfusion bioreactor system) to achieve a steady state viable cell concentration, where the steady state viable cell concentration is within a range of $20\times10^6$ cells/mL to $15\times10^7$ cells/mL and where the bioreactor system includes at least 25 L of culture media and a gas exit velocity that is at most 20 m/s. In some embodiments, a bioreactor system has a gas exit velocity that is controlled at a rate of about 15 m/s or less, 14 m/s or less, 13 m/s or less, 12 m/s or less, 11 m/s or less, 10 m/s or less, 9 m/s or less, or 8 m/s or less. In some embodiments, a bioreactor system includes a sparger. In some embodiments, a sparger has a gas exit velocity that is controlled at a rate of about 15 m/s or less, 14 m/s or less, 13 m/s or less, 12 m/s or less, 11 m/s or less, 10 m/s or less, 9 m/s or less, or 8 m/s or less.

In some instances, provided are methods including culturing shear-sensitive cells in a bioreactor system (e.g., a perfusion bioreactor system) that comprises at least 25 L of culture media, wherein the bioreactor system has a gas exit velocity that is at most 20 m/s, and wherein the shear-sensitive cells are present at a steady state viable cell concentration within a range of about $20\times10^6$ cells/mL to about $15\times10^7$ cells/mL. In some embodiments, a bioreactor system (e.g., a perfusion bioreactor system) has a gas exit velocity that is 15 m/s or less, 14 m/s or less, 13 m/s or less, 12 m/s or less, 11 m/s or less, 10 m/s or less, 9 m/s or less, or 8 m/s or less. In some embodiments, the gas exit velocity is controlled throughout the culturing step. In some embodiments, the gas exit velocity is controlled at least until the bioreactor system reaches a steady state condition.

In some instances, provided are methods of culturing a population of cells consisting of shear-sensitive cells in a bioreactor system with at least 25 L (e.g., at least 200 L) of culture media and a gas exit velocity that is at most 20 m/s (e.g., at most 10 m/s) to achieve a steady state viable cell concentration in the culture media within a range of $20\times10^6$ cells/mL to $15\times10^7$ cells/mL. In some embodiments, a steady state viable cell concentration is a viable cell concentration that varies at most 20% over a period of 5 days.

In some instances, provided are continuous culture process for culturing a population of cells consisting of shear-sensitive cells, including controlling gas exit velocity of a bioreactor system so that the gas exit velocity does not exceed a rate of 20 m/s, where the bioreactor system comprises at least 25 L of culture media, and where the population of cells achieves a steady state viable cell concentration within a range of $20\times10^6$ cells/mL to 15×107 cells/mL. In some embodiments, gas exit velocity is controlled at a rate of about 15 m/s or less, 14 m/s or less, 13 m/s or less, 12 m/s or less, 11 m/s or less, 10 m/s or less, 9 m/s or less, or 8 m/s or less. In some embodiments, a bioreactor system includes a sparger. In some embodiments, sparger gas exit velocity is controlled at a rate of about 15 m/s or less, 14 m/s or less, 13 m/s or less, 12 m/s or less, 11 m/s or less, 10 m/s or less, 9 m/s or less, or 8 m/s or less.

In some embodiments, gas exit velocity is controlled for at least part of duration that shear-sensitive cells are cultured. In some embodiments, control of gas exit velocity initiates when a population of cells (e.g. a population of shear-sensitive cells, e.g., an inoculate) is added to a bioreactor system (e.g., when a population of cells is combined with a culture media of a bioreactor system). In some embodiments, control of gas exit velocity initiates about 2 hours, 6 hours, 12 hours, 24 hours, or 48 hours after a population of cells (e.g. a population of shear-sensitive cells, e.g., an inoculate) is added to a bioreactor system (e.g., when a population of cells is combined with a culture media of a bioreactor system).

In some embodiments, control of gas exit velocity initiates during a culturing process when the cells being culture reach a particular density. In some embodiments, control of gas exit velocity initiates when a bioreactor system has a concentration of shear-sensitive cells that is at least $1\times10^6$ cells/mL, $2\times10^6$ cells/mL, $5\times10^6$ cells/mL, or $10\times10^6$ cells/mL. I In some embodiments, gas exit velocity is controlled at least until the bioreactor system reaches a steady state condition. In some embodiments, a steady state condition includes having a viable cell concentration that varies at most 20% over a period of 5 days. In some embodiments, gas exit velocity is controlled from such time that a population of cells (e.g. a population of shear-sensitive cells, e.g., an inoculate) is added to a bioreactor system (e.g., when a population of cells is combined with a culture media of a bioreactor system) until the culture reaches a steady state condition (e.g., having a viable cell concentration that varies at most 20% over a period of 5 days). In some embodiments, gas exit velocity is controlled from such time that a bioreactor system has a concentration of shear-sensitive cells that is at least $1 \times 10^6$ cells/mL until the culture reaches a steady state condition (e.g., having a viable cell concentration that varies at most 20% over a period of 5 days).

In some embodiments, gas exit velocity is controlled throughout a culturing step. In some embodiments, gas exit velocity is controlled for at least about 10 days, at least about 15 days, at least about 20 days, at least about 25 days, at least about 30 days, at least about 40 days, at least about 50 days, or at least about 60 days of culturing. In some embodiments, gas exit velocity is controlled from such time that a population of cells (e.g. a population of shear-sensitive cells, e.g., an inoculate) is added to a bioreactor system (e.g., when a population of cells is combined with a culture media of a bioreactor system) and continues for at least about 10 days, at least about 15 days, at least about 20 days, at least about 25 days, at least about 30 days, at least about 40 days, at least about 50 days, or at least about 60 days of culturing. In some embodiments, gas exit velocity is controlled from such time that a bioreactor system has a concentration of shear-sensitive cells that is at least $1 \times 10^6$ cells/mL until the culture reaches a steady state condition (e.g., having a viable cell concentration that varies at most 20% over a period of 5 days) and continues for at least about 10 days, at least about 15 days, at least about 20 days, at least about 25 days, at least about 30 days, at least about 40 days, at least about 50 days, or at least about 60 days of culturing.

In some instances, provided are perfusion culture processes for culturing shear-sensitive cells, comprising: controlling gas exit velocity of a perfusion bioreactor system so that the gas exit velocity does not exceed a rate of 20 m/s, wherein the perfusion bioreactor system comprises at least 25 L of culture media, wherein the culture media includes shear-sensitive cells, and wherein the shear-sensitive cells are present at a steady state viable cell concentration within a range of about $20 \times 10^6$ cells/mL to about $15 \times 10^7$ cells/mL. In some embodiments, gas exit velocity of a perfusion bioreactor system is controlled to not exceed a rate of 10 m/s.

In some embodiments, a steady-state viable cell concentration of shear-sensitive cells is in an amount within a range bounded by a lower limit and an upper limit, the upper limit being larger than the lower limit. In some embodiments, the lower limit may be about $20 \times 10^6$ cells/mL, about $25 \times 10^6$ cells/mL, about $30 \times 10^6$ cells/mL, about $35 \times 10^6$ cells/mL, about $40 \times 10^6$ cells/mL, about $45 \times 10^6$ cells/mL, about $50 \times 10^6$ cells/mL, about $60 \times 10^6$ cells/mL, about $70 \times 10^6$ cells/mL, about $80 \times 10^6$ cells/mL, or about $90 \times 10^6$ cells/mL. In some embodiments, the upper limit may be about $40 \times 10^6$ cells/mL, about $45 \times 10^6$ cells/mL, about $50 \times 10^6$ cells/mL, about $60 \times 10^6$ cells/mL, about $70 \times 10^6$ cells/mL, about $80 \times 10^6$ cells/mL, about $90 \times 10^6$ cells/mL, about $10 \times 10^7$ cells/mL, about $11 \times 10^7$ cells/mL, about $12 \times 10^7$ cells/mL, about $13 \times 10^7$ cells/mL, about $14 \times 10^7$ cells/mL or about $15 \times 10^7$ cells/mL.

In some embodiments, a perfusion bioreactor system has a controlled level of dissolved carbon dioxide. In some embodiments, a culture media includes a level of dissolved carbon dioxide that is 120 mmHg or less, 115 mmHg or less, 110 mmHg or less, 105 mmHg or less, 100 mmHg or less, 95 mmHg or less, 90 mmHg or less, 85 mmHg or less, or 80 mm Hg or less.

In some certain embodiments, a perfusion bioreactor system has a gas exit velocity that is 10 m/s or less; and includes a level of dissolved carbon dioxide that is 80 mmHg or less.

In some embodiments, a cell culture system has a level of dissolved carbon dioxide that is 120 mmHg or less. In some embodiments, a continuous cell culture system (e.g., perfusion cell culture system) has a level of dissolved carbon dioxide within a range of about 20 mmHg to about 120 mmHg. In some embodiments, dissolved carbon dioxide is present in a continuous cell culture media in an amount within a range bounded by a lower limit and an upper limit, the upper limit being larger than the lower limit. In some embodiments, the lower limit may be about 20 mmHg, about 30 mmHg, about 40 mmHg, about 50 mmHg, about 60 mmHg, or about 70 mmHg. In some embodiments, the upper limit may be about 50 mmHg, about 60 mmHg, about 70 mmHg, about 80 mmHg, about 90 mmHg, about 100 mmHg, about 110 mmHg, or about 120 mmHg.

In some embodiments, a perfusion bioreactor system includes at least 50 L, at least 100 L, at least 200 L, at least 500 L, at least 1,000 L, or at least 2,000 L of culture media.

In some embodiments, continuous culturing of shear-sensitive cells is performed for a duration of at least 10 days. In some embodiments, continuous culturing of shear-sensitive cells is performed for a duration of about 30 days to about 60 days.

In some embodiments, continuous culturing of shear-sensitive cells is performed for a duration within a range of 10 days to 180 days. In some embodiments, continuous culturing of shear-sensitive cells is performed for an amount of time within a range bounded by a lower limit and an upper limit, the upper limit being larger than the lower limit. In some embodiments, the lower limit may be about 10 days, about 15 days, about 20 days, about 25 days, about 30 days, about 35 days, about 40 days, about 50 days, or about 60 days. In some embodiments, the upper limit may be about 30 days, about 35 days, about 40 days, about 50 days, about 60 days, about 70 days, about 80 days, about 90 days, about 100 days, about 120 days, about 140 days, about 160 days, or about 180 days.

In some embodiments, a method of continuous culture of the present disclosure includes a step of measuring the viable cell concentration. In some embodiments, a measured viable cell concentration is at least $30 \times 10^6$ cells/mL, at least $40 \times 10^6$ cells/mL, or at least $50 \times 10^6$ cells/mL.

In some embodiments, shear-sensitive cells for culturing in accordance with the present disclosure are mammalian cells.

In some embodiments, a shear-sensitive cell is mammalian cell. In some embodiments, a shear-sensitive cell is a murine cell. In some embodiments, a shear-sensitive cell is from a mouse cell line. In some embodiments, a shear-sensitive cell line is a mouse myeloma cell lines. In some certain embodiments, shear-sensitive cells are selected from:

NS0 cells and SP 2/0 cells. In some certain embodiments, shear-sensitive cells for use in accordance with the present disclosure are SP 2/0 cells.

In some embodiments, a shear-sensitive cell is human cell. In some embodiments, a human shear-sensitive cell line is selected from: HEK 293: human embryonic kidney 293; HT-1080: from a fibrosarcoma with an epithelial-like phenotype; PER.C6: from human embryonic retinal cells immortalized via transfection with the adenovirus E1 gene; CAP: from human amniocytes immortalized through an adenovirus type 5 E1 gene; HKB-11: created through polyethylene glycol fusion of HEK293-S and a human B-cell line; and HuH-7: from a human hepatocellular carcinoma. In some certain embodiments, shear-sensitive cells are selected from: HEK 293 cells, fibrosarcoma HT 1080 cells, PER.C6 cells, CAP cells, HKB-11 cells and HuH-7 cells.

In some embodiments, shear-sensitive cells for use in accordance with the present disclosure are engineered to include or express a cell product. In some embodiments, cultured shear-sensitive cells include or express a cell product. In some embodiments, a cell product is or includes a nucleic acid, a lipid, a peptide, and/or a protein. In some embodiments, a cell product is a recombinant protein. In some embodiments, a recombinant protein is a glycoprotein. In some embodiments, a glycoprotein is an Fc-containing glycoprotein. In some embodiments, a glycoprotein is an antibody agent. In some embodiments, an antibody agent is a monoclonal antibody. In some certain embodiments, a monoclonal antibody is ustekinumab.

In some embodiments, a shear-sensitive cell of the present disclosure includes a nucleic acid that encodes an antibody agent that has been approved, e.g., under a secondary approval process, for therapeutic or diagnostic use in humans or animals. In some certain embodiments, a shear-sensitive cell of the present disclosure includes a nucleic acid that encodes ustekinumab.

In some embodiments, a method and/or process of the present disclosure includes isolating a cell product from at least a portion of the cells and/or isolating a cell product from at least a portion of the culture media. In some embodiments, a cell product is a recombinant protein, e.g., a glycoprotein, e.g., an Fc-containing glycoprotein, e.g., an antibody agent, e.g., a monoclonal antibody.

In some embodiments, a cell culture media also includes an antifoam agent (e.g., antifoam C) at a concentration within a range of 1 ppm to 500 ppm. In some embodiments, shear-sensitive cells are cultured in a cell culture media that includes a shear-force protectant (e.g., Pluronic F-68). In some embodiments, shear-sensitive cells (e.g., a population of shear-sensitive cells) are cultured in a cell culture media that includes Pluronic F-68 at a concentration within a range of 1 g/L to 15 g/L. In some embodiments, a population of shear-sensitive cells is cultured in culture media that includes an antifoam agent (e.g., antifoam C) at a concentration within a range of 1 ppm to 500 ppm and a shear-force protectant (e.g., Pluronic F-68) at a concentration within a range of 1 g/L to 15 g/L.

In some embodiments, a perfusion bioreactor system includes a bioreactor tank. In some embodiments, a bioreactor tank is a stirred bioreactor tank. In some embodiments, a bioreactor tank has a capacity of at least 50 L, 100 L, 200 L, 250 L, 400 L, 500 L, 600 L, 800 L, 1,000 L, or 2,000 L. In some certain embodiments, a bioreactor tank has a capacity of about 200 L, about 250 L, or more.

In some embodiments, a bioreactor system (e.g., a perfusion bioreactor system) includes a cell retention device. In some embodiments, a cell retention device is or includes a continuous centrifuge, an alternating tangential flow filter (ATF), a tangential flow membrane filter (TFF), a dynamic filter, a spin-filter, an ultrasonic and dielectrophoretic separator, or a gravity settler. In some certain embodiments, a cell retention device is or includes an ATF.

In some embodiments, a bioreactor system includes a stirred-tank bioreactor, a cell retention device, a media supply, and a bleed waste collection.

In some embodiments, a bioreactor system (e.g., a perfusion bioreactor system) includes a sparger. In some embodiments, a bioreactor system includes a drilled hole sparger. In some embodiments, a bioreactor system includes an open pipe sparger. In some embodiments, a bioreactor system includes a sintered sparger.

In some instances, provided are methods of large-scale (e.g., at least 25 L, e.g., at least 100 L) continuous culturing of shear-sensitive cells that include: providing or obtaining shear-sensitive cells that comprise a recombinant protein-encoding nucleic acid, and culturing the cells in a bioreactor system with a controlled gas exit velocity and under conditions sufficient for expression of the recombinant protein. In some embodiments, a bioreactor system has a gas exit velocity that controlled at a rate of at most 20 m/s (e.g., about 5 m/s to about 10 m/s) until the system reaches steady-state conditions. In some embodiments, a bioreactor system has a gas exit velocity that controlled at a rate of at most 20 m/s (e.g., about 5 m/s to about 10 m/s) throughout the culturing. In some embodiments, viable cell concentration at steady-state conditions is within a range of about $20\times10^6$ cells/mL to about $15\times10^7$ cells/mL. In some embodiments, viable cell concentration at steady-state conditions is at least $40\times10^6$ cells/mL.

In some instances, provided are methods of producing a protein preparation continuous culturing of shear-sensitive cells that include: continuously culturing the shear-sensitive cells in a bioreactor system with a controlled gas exit velocity. In some embodiments, a bioreactor system includes a bioreactor tank with a capacity that is at least 25 L, at least 100 L, or at least 200 L. In some embodiments, the gas exit velocity that controlled at a rate of at most 20 m/s (e.g., about 5 m/s to about 10 m/s) until the system reaches steady-state conditions. In some embodiments, the bioreactor system has a gas exit velocity that controlled at a rate of at most 20 m/s (e.g., about 5 m/s to about 10 m/s) throughout the culturing. In some embodiments, viable cell concentration at steady-state conditions is within a range of about $20\times10^6$ cells/mL to about $15\times10^7$ cells/mL. In some embodiments, viable cell concentration at steady-state conditions is at least $40\times10^6$ cells/mL. In some embodiments, methods of producing a protein preparation include isolating the protein or mixture of proteins from the cells and/or cell media.

These, and other aspects of the invention, are described in more detail below and in the claims.

BRIEF DESCRIPTION OF THE DRAWING

The Drawing included herein, which is composed of the following Figures, is for illustration purposes only and not for limitation.

FIG. 5 depicts several continuous cell culture runs with 3 L perfusion bioreactors were performed with various gas exit velocities (GEVs). Top panel shows viable cell concentration (VCC) over time and bottom panel shows percent viability over time. FU27 (diamonds) represents control sample. FU28 (open squares) represents GEV at 10 m/s until day 9 and then at 16 m/s from thereon. FU29 (open triangles) represents GEV at 13 m/s and culture crashed on day 12. FU30 (X's) represents GEV at 16 m/s until day 9 and then decreased to 10 m/s from thereon.

FIG. 6 depicts viable cell concentration (in 106 cells/mL) (top panel) and percent viability (bottom panel) of exemplary shear-sensitive cells (e.g., SP2/0 cells) cultured in perfusion culture systems with different levels of dissolved $CO_2$.

FIG. 7A and FIG. 7B depict comparison of continuous culture performances of shear-sensitive cells at different scales while controlling GEV and dissolved $CO_2$. Top panel of FIG. 7A shows viable cell concentration (VCC) over and bottom panel of FIG. 7A shows percent viability over time. Top panel of FIG. 7B shows gas exit velocity over time and bottom panel of FIG. 7B shows dissolved $CO_2$ over time.

FIG. 8 provides tables summarizing predicted models for 250 L cultures (e.g., using a SUB250 bioreactor system) for different parameters.

FIG. 9 depicts total glycan levels (top panel) and sialic acid content (bottom panel) for continuous cell cultures of shear-sensitive cells at different scales. Left most bars for each represent 3 L culture process, middle bars for each represent 100 L culture process and right most bars represent 250 L culture process.

FIG. 11 provides a table summarizing predicted models for 1000 L cultures (e.g., using a SUB1000 bioreactor system) for different parameters.

FIG. 12 provides an exemplary equation for determining gas exit velocity.

CERTAIN DEFINITIONS

Figure 1:
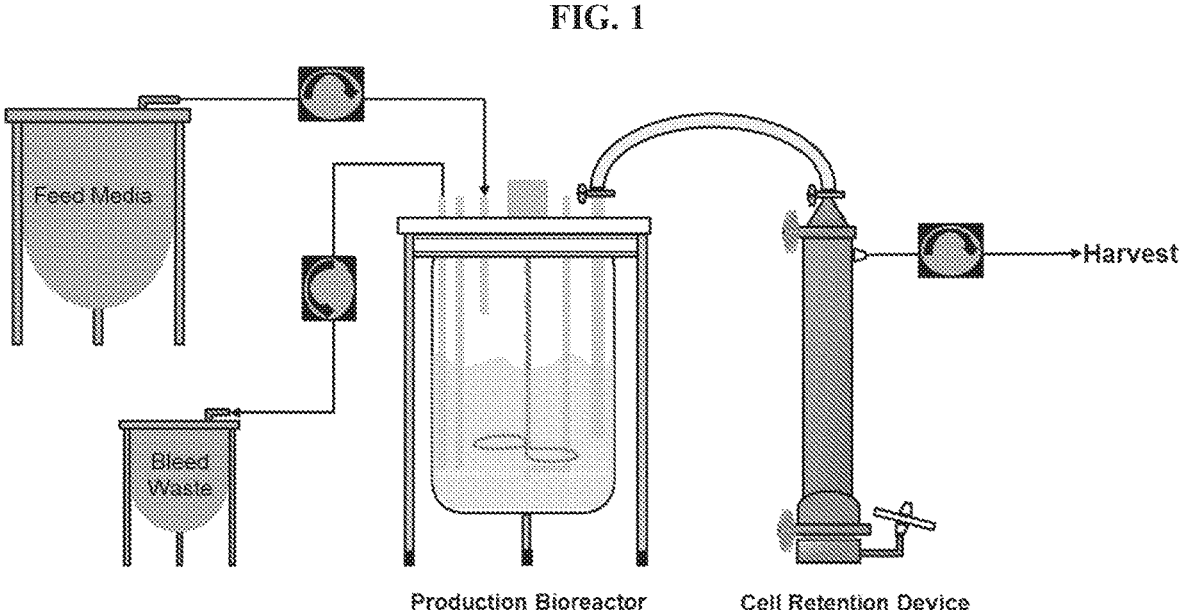
FIG. 1 depicts an exemplary schematic of a perfusion culture system with an exemplary alternating tangential flow as a cell retention device. As shown, an exemplary perfusion culture system can include a production bioreactor (e.g., a stirred bioreactor tank), a cell retention device (e.g., alternating tangential flow), a feed media supply, and a bleed waste.

In general, terminology used herein is in accordance with its understood meaning in the art, unless clearly indicated otherwise. Explicit definitions of certain terms are provided below; meanings of these and other terms in particular instances throughout this specification will be clear to those skilled in the art from context.

References cited within this specification, or relevant portions thereof, are incorporated herein by reference.

In order that the present invention may be more readily understood, certain terms are first defined below. Additional definitions for the following terms and other terms are set forth throughout the specification.

As used herein, the terms "about" or "approximately," as applied to one or more values of interest, refers to a value that is similar to a stated reference value. In certain embodiments, the terms "about" or "approximately" refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

As used herein, the term "antibody," has its art understood meaning and refers to an immunoglobulin (Ig) that binds specifically to a particular antigen. As is known by those of ordinary skill in the art, antibodies produced in nature are typically comprised of four polypeptide chains, two heavy (H) chains and two light (L) chains. Each heavy and light chain is comprised of a variable region (abbreviated herein as HCVR or $V_H$ and LCVR or $V_L$, respectively) and a constant region. The constant region of a heavy chain comprises a $C_H1$, $C_H2$ and $C_H3$ domain (and optionally a $C_H4$ domain in the case of IgM and IgE). The constant region of a light chain is comprised of one domain, CL. The $V_H$ and $V_L$ regions further contain regions of hypervariability, termed complementarity determining regions (CDRs), interspersed with regions that are more conserved, which are termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgM, IgD, IgG, IgA and IgE), class (e.g., IgG1, IgG2, IgG3, IgG4, IgA1 and IgA2) or subclass.

As used herein, the term "antibody agent" refers to an agent that specifically binds to a particular antigen. In some embodiments, the term encompasses any polypeptide with immunoglobulin structural elements sufficient to confer specific binding. In various embodiments, suitable antibody agents may include, but are not limited to, monoclonal antibodies, polyclonal antibodies, humanized antibodies, primatized antibodies, chimeric antibodies, human antibodies, bi-specific or multi-specific antibodies, single domain antibodies (e.g., shark single domain antibodies (e.g., IgNAR or fragments thereof)), conjugated antibodies (i.e., antibodies conjugated or fused to other proteins, radiolabels, cytotoxins, etc.), Small Modular ImmunoPharmaceuticals ("SMIPs™"), single chain antibodies, cameloid antibodies, antibody fragments, etc. In some embodiments, the term can refer to a stapled peptide. In some embodiments, the term can refer to an antibody-like binding peptidomimetic. In some embodiments, the term can refer to an antibody-like binding scaffold protein. In some embodiments, the term can refer to monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments, an included CDR is substantially identical to a reference CDR in that it is either identical in sequence or contains between 1 to 5 amino acid substitutions as compared with the reference CDR. In some embodiments, an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments, an included CDR is substantially identical to a reference CDR in that it shows at least 96%, 96%, 97%, 98%, 99%, or 100% sequence identity with the reference CDR. In some embodiments, an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments, an included CDR is substantially identical to a reference CDR in that 1 to 5 amino acids within the included CDR are deleted, added, or substituted as compared with the reference CDR but the included CDR has an amino acid sequence that is otherwise identical to the reference CDR. In some embodiments, an included CDR is substantially identical to a reference CDR in that at least one amino acid within the included CDR is substituted as compared with the reference CDR but the included CDR has an amino acid sequence that is otherwise identical with that of the reference CDR. In some embodiments, an included CDR is substantially identical to a reference CDR in that 1 to 5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain, which is homologous or largely homologous to an immunoglobulin-binding domain. In some embodiments, an antibody agent is or comprises a polypeptide that includes all CDRs found in a particular reference antibody chain or chains (e.g., heavy chain and/or light chain).

As used herein, the terms "biologic", "biotherapeutic", and "biologic product" are used interchangeably to refer to polypeptide and protein products. For example, biologics herein include naturally derived or recombinant products expressed in cells, such as, e.g., proteins, glycoproteins, fusion proteins, growth factors, vaccines, blood factors, thrombolytic agents, hormones, interferons, interleukin based products, antibody agents, (e.g., monoclonal antibodies, bispecific antibodies, etc.), and therapeutic enzymes. Some biologics are approved under a "Biologics License Application" or "BLA", under section 351 (a) of the Public Health Service (PHS) Act, whereas biosimilar and interchangeable biologics referencing a BLA as a reference product are licensed under section 351 (k) of the PHS Act.

Section 351 of the PHS Act is codified as 42 U.S.C. 262. Other biologics may be approved under section 505 (b) (1) of the Federal Food and Cosmetic Act, or as abbreviated applications under sections 505 (b) (2) and 505 (j) of the Hatch Waxman Act, wherein section 505 is codified 21 U.S.C. 355.

As used herein, "gas exit velocity" refers to a rate of gas exit from a gas source of a bioreactor system, e.g., a gas source for aeration (e.g., supplying air and/or oxygen) of culture media. In some embodiments, gas exit velocity refers to the rate that gas exits from one or more gas source opening(s) (e.g., holes) and enters culture media. In some embodiments, gas exit velocity is calculated using an equation as provided in FIG. 12. In some embodiments, a bioreactor system includes a sparger and gas exit velocity refers to rate of gas exit from one more more sparger opening(s) (e.g., holes). In some embodiments, a bioreactor system includes a sparger and gas exit velocity refers to an average of the rates of gas exit from the openings of said sparger.

As used herein, a "glycoprotein" refers to an amino acid sequence that includes one or more oligosaccharide chains (e.g., glycans) covalently attached thereto. Exemplary amino acid sequences include peptides, polypeptides and proteins. Exemplary glycoproteins include glycosylated antibodies, antibody agents, and antibody-like molecules (e.g., Fc fusion proteins). Exemplary antibodies include monoclonal antibodies and/or fragments thereof, polyclonal antibodies and/or fragments thereof, and Fc domain containing fusion proteins (e.g., fusion proteins containing the Fc region of IgG1, or a glycosylated portion thereof).

The term "isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

As used herein "recovering," refers to the process of rendering an agent or entity substantially free of other previously-associated components, for example by isolation, e.g., using purification techniques known in the art. In some embodiments, an agent or entity is recovered from a natural source and/or a source comprising cells.

In general, a "protein", as used herein, is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

The term "protein preparation" as used herein refers to a mixture of proteins obtained according to a particular production method. Proteins in a protein preparation may be the same or different, i.e., a protein preparation may include multiple copies of the same protein and/or a mixture of different proteins. In some embodiments, a protein preparation includes glycoprotein preparations. A glycoprotein preparation is a composition or mixture that includes at least one glycoprotein. In some instances, a glycoprotein preparation includes multiple copies of the same protein (i.e., having the same amino acid sequence) but have a mixture of glycans associated with the protein. In some instances, a glycoprotein preparation is prepared using a method and/or system as provided herein. Production methods can include a recombinant preparation step using cultured cells that have been engineered to express the proteins in the protein preparation (or to express the proteins at a relevant level or under relevant conditions). In some embodiments, a production method may include an isolation step in which proteins are isolated from certain components of the engineered cells (e.g., by lysing the cells and pelleting the protein component by centrifugation). In some embodiments, production method may also include a purification step in which the proteins in the protein preparation are separated (e.g., by chromatography) from other cellular components, e.g., other proteins or organic components that were used in earlier steps. It will be appreciated that these steps are non-limiting and that any number of additional productions steps may be included. Different protein preparations may be prepared by the same production method but on different occasions (e.g., different runs or preparations). Alternatively, different protein preparations may be prepared by different production methods. Two production methods may differ in any way (e.g., expression vector, engineered cell type, culture conditions, isolation procedure, purification conditions, etc.).

As used herein, "sample(s)" refer to separately procured samples. In some embodiments, evaluation of separate samples includes evaluation of samples from the same culture run (e.g., at different time points during preparation) or from different culture runs (e.g., different rounds of culture).

As used herein, "sparging" or "gas sparging" refer to aeration or addition of gas (e.g., air and/or O2) to a cell culture media. Generally, gas sparging refers to a process of bubbling gas directly into a culture medium (e.g., by way of a sparger). In some embodiments, sparging is used to achieve a dissolved O2 concentration of at least about 20%, or between about 20% to about 100%.

As used herein, "steady state" or "steady state conditions" as used in reference to a cell culture system or process means that cell culture has a viable cell concentration that varies at most 20% over a period of at least 5 days (e.g., 5 days to about 60 days). In some embodiments, a cell culture system has a viable cell concentration that varies at most 20% over a period of 5 days. In some embodiments, a cell culture system has a viable cell concentration that varies at most 15%, at most 10%, or at most 5% over a period of at least 5 days (e.g., 5 days, 10 days, 15 days, 20 days, 25 days, 30 days, 40 days, 50 days, 60 days). In some embodiments, a cell culture system has a viable cell concentration that varies at most 15%, at most 10%, or at most 5% over a period of 5 days. In some embodiments, a cell culture system has a viable cell concentration of shear-sensitive cells that varies at most 10% (i.e., within a range of plus or minus 10%) over a period of at least 5 days (e.g., 5 days, 10 days, 15 days, 20 days, 25 days, 30 days, 40 days, 50 days, 60 days). In some embodiments, a cell culture system has a viable cell concentration of shear-sensitive cells that varies at most 10% (i.e., within a range of plus or minus 10%) over a period of 5 days. In some embodiments, a steady state viable cell concentration is achieved and/or maintained through bleeding a bioreactor systems (e.g., removal of excess cells).

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls. The section headings used herein are for organizational purposes only and are not to be construed as limiting the subject matter described in any way.

DETAILED DESCRIPTION OF CERTAIN EMBODIMENTS

The present disclosure identifies and addresses, in part, a problem with current continuous cell culture techniques (e.g., perfusion cell culture) in that at large culture volumes (e.g., at least 100 L, e.g., at least 200 L), certain cells have insufficient viable cell concentrations and impaired cell viability. The present disclosure encompasses a recognition that scale up of high cell density continuous cell culture process can be challenging due to its high demand for oxygen supply and dissolved carbon dioxide (pCO$_2$) removal. The present disclosure analyzed a number of different variables associated with large-scale continuous cell culture.

The present disclosure encompasses a recognition that the importance of aeration increases with bioreactor volume and cell concentration. In particular, the present disclosure provides the insight that controlling gas exit velocity of a bioreactor system can improve the performance of large-scale continuous culturing of certain cells (such as, e.g., shear-sensitive cells).

In some embodiments, the present disclosure provides methods and processes for large-scale (e.g., at least 100 L, e.g., at least 200 L) continuous culture (e.g., perfusion culture) of shear-sensitive cells, where the gas exit velocity of the bioreactor system is controlled and/or maintained within a defined amount and/or range. For example, provided are methods of large-scale culture of shear-sensitive cells in a bioreactor system (e.g., a perfusion bioreactor system) with a gas exit velocity that is at most 20 m/s (e.g., at most 10 m/s). The provided methods permit generation of high density cell cultures (e.g., having a steady state viable cell concentration within a range of $20 \times 10^6$ cells/mL to $15 \times 10^7$ cells/mL).

Continuous Culture Methods and Processes

The present disclosure provides, in part, methods, processes, and/or systems for large-scale (e.g., at least 25 L, e.g., at least 100 L, e.g., at least 200 L) continuous culture (e.g., perfusion cell culture) of shear-sensitive cells (e.g., a population of cells comprising shear-sensitive cells, e.g., a population of cells consisting of shear-sensitive cells). In some embodiments, a large-scale culture is 25 L to 3,000 L. In some embodiments, a large-scale culture is 25 L, 50 L, 100 L, 200 L, 250 L, 400 L, 500 L, 600 L, 800 L, 1000 L, 1200 L, 1500 L, 2000 L, 3000 L or greater. In some embodiments, large-scale culture is 100 L or greater. In some certain embodiments, a large-scale culture is 200 L or greater. In some certain embodiments, a large-scale culture is 250 L or greater.

In some instances, a continuous cell culture system (e.g., perfusion cell culture system) is a large-scale culture (e.g., 200 L or greater) that can produce a high density of shear-sensitive cells (e.g., a steady state viable cell concentration that is e.g., at least $20 \times 10^6$ cells/mL, e.g., at least $30 \times 10^6$ cells/mL, e.g., at least $40 \times 10^6$ cells/mL).

In some instances, a method, process and/or system of continuous cell culture system has and/or achieves a steady-state viable cell concentration of shear-sensitive cells that is within a range of about $20 \times 10^6$ cells/mL to about $15 \times 10^7$ cells/mL. In some embodiments, a steady-state viable cell concentration of shear-sensitive cells is in an amount within a range bounded by a lower limit and an upper limit, the upper limit being larger than the lower limit. In some embodiments, the lower limit may be about $20 \times 10^6$ cells/mL, about $25 \times 10^6$ cells/mL, about $30 \times 10^6$ cells/mL, about $35 \times 10^6$ cells/mL, about $40 \times 10^6$ cells/mL, about $45 \times 10^6$ cells/mL, about $50 \times 10^6$ cells/mL, about $60 \times 10^6$ cells/mL, about $70 \times 10^6$ cells/mL, about $80 \times 10^6$ cells/mL, or about $90 \times 10^6$ cells/mL. In some embodiments, the upper limit may be about $40 \times 10^6$ cells/mL, about $45 \times 10^6$ cells/mL, about $50 \times 10^6$ cells/mL, about $60 \times 10^6$ cells/mL, about $70 \times 10^6$ cells/mL, about $80 \times 10^6$ cells/mL, about $90 \times 10^6$ cells/mL, about $10 \times 107$ cells/mL, about $11 \times 10^7$ cells/mL, about $12 \times 10^7$ cells/mL, about $13 \times 10^7$ cells/mL, about $14 \times 10^7$ cells/mL or about $15 \times 10^7$ cells/mL.

Generally, cell culture methods of the present disclosure including culturing at a temperature within a range of 25° C. to 40° C. and with gravity as it is encountered on earth.

In some embodiments, a continuous cell culture system (e.g., perfusion cell culture system) has a gas exit velocity that is within a range of about 1 m/s to about 20 m/s. In some embodiments, a continuous cell culture system (e.g., perfusion cell culture system) has a gas exit velocity that is within a range of about 1 m/s to about 10 m/s. In some embodiments, a continuous cell culture system (e.g., perfusion cell culture system) has a gas exit velocity that does not exceed 20 m/s. In some embodiments, a continuous cell culture system (e.g., perfusion cell culture system) has a gas exit velocity that does not exceed 10 m/s.

In some embodiments, a continuous cell culture system (e.g., perfusion cell culture system) has a gas exit velocity at a rate within a range bounded by a lower limit and an upper limit, the upper limit being larger than the lower limit. In some embodiments, the lower limit may be about 1 m/s, about 2 m/s, about 3 m/s, about 4 m/s, about 5 m/s, about 6 m/s, about 7 m/s, about 8 m/s, about 9 m/s or about 10 m/s. In some embodiments, the upper limit may be about 5 m/s, about 6 m/s, about 7 m/s, about 8 m/s, about 9 m/s, about 10 m/s, about 11 m/s, about 12 m/s, about 13 m/s, about 14 m/s, about 15 m/s, about 16 m/s, about 18 m/s, or about 20 m/s.

In some embodiments, a continuous cell culture system (e.g., perfusion cell culture system) has a level of dissolved carbon dioxide that does not exceed 120 mmHg. In some embodiments, a continuous cell culture system (e.g., perfusion cell culture system) has a level of dissolved carbon dioxide within a range of about 20 mmHg to about 120 mmHg. In some embodiments, dissolved carbon dioxide is present in a continuous cell culture media in an amount within a range bounded by a lower limit and an upper limit, the upper limit being larger than the lower limit. In some embodiments, the lower limit may be about 20 mmHg, about 30 mmHg, about 40 mmHg, about 50 mmHg, about 60 mmHg, or about 70 mmHg. In some embodiments, the upper limit may be about 50 mmHg, about 60 mmHg, about 70 mmHg, about 80 mmHg, about 90 mmHg, about 100 mmHg, about 110 mmHg, or about 120 mmHg.

In some embodiments, continuous culturing of shear-sensitive cells (e.g., a population of cells comprising shear-sensitive cells, e.g., a population of cells consisting of shear-sensitive cells) is performed for a duration within a range of about 10 days to about 180 days. In some embodiments, continuous culturing of shear-sensitive cells (e.g., a population of cells comprising shear-sensitive cells, e.g., a population of cells consisting of shear-sensitive cells) is performed for an amount of time within a range bounded by a lower limit and an upper limit, the upper limit being larger than the lower limit. In some embodiments, the lower limit may be about 10 days, about 15 days, about 20 days, about 25 days, about 30 days, about 35 days, about 40 days, about 50 days, or about 60 days. In some embodiments, the upper limit may be about 30 days, about 35 days, about 40 days, about 50 days, about 60 days, about 70 days, about 80 days, about 90 days, about 100 days, about 120 days, about 140 days, about 160 days, or about 180 days.

In some embodiments, continuous culturing of shear-sensitive cells (e.g., a population of cells comprising shear-sensitive cells, e.g., a population of cells consisting of shear-sensitive cells) is performed for a duration of at least 10 days. In some embodiments, continuous culturing of shear-sensitive cells (e.g., a population of cells comprising shear-sensitive cells, e.g., a population of cells consisting of shear-sensitive cells) is performed for a duration of about 30 to about 60 days.

Bioreactor Systems

The present disclosure provides bioreactor systems for large-scale continuous cell culture, such as for culturing shear-sensitive cells (e.g., a population of cells comprising shear-sensitive cells, e.g., a population of cells consisting of shear-sensitive cells). Bioreactor systems of the present disclosure are suitable for continuous culture methods. In some embodiments, a bioreactor system of the present disclosure is suitable for perfusion culture. An exemplary schematic of a bioreactor system suitable for culture methods of the present disclosure is depicted in FIG. 1. In some embodiments, a bioreactor system includes a bioreactor tank and a cell retention device. In some embodiments, a bioreactor system, includes a bioreactor tank, a cell retention device, a media supply, and a bleed waste collection. In some embodiments, a bioreactor system further includes a population of cells (e.g., a population of cells consisting of shear-sensitive cells, e.g., an inoculate) and a cell culture media.

In some embodiments, a bioreactor system includes a stirred tank bioreactor. In some embodiments, a bioreactor tank (e.g., of a stirred tank bioreactor) has a capacity within a range of 25 L to 3,000 L. In some embodiments, a bioreactor tank (e.g., of a stirred tank bioreactor) has a capacity of at least 25 L, 50 L, 100 L, 200 L, 250 L, 300 L, 400 L, 500 L, 600 L, 800 L, 1000 L, 1200 L, 1400 L, 1500 L, 1600 L, 1800 L, 2000 L, 2400 L, 2500 L, 2600 L, 2800 L, or 3000 L. In some embodiments, a stirred tank bioreactor has a capacity that is at least 100 L. In some embodiments, a stirred tank bioreactor has a capacity that is at least 200 L. In some embodiments, a stirred tank bioreactor has a capacity that is at least 250 L. In some embodiments, a stirred tank bioreactor has a capacity that is at least 500 L. In some embodiments, a stirred tank bioreactor has a capacity that is at least 1000 L.

In some embodiments, a bioreactor system includes a sparger. In general a sparger can be used to introduce air and/or oxygen into a cell culture media. The present disclosure encompasses a recognition that sparger selection can influence the rate and extent of aeration and also to minimize foaming. In some embodiments, a bioreactor system includes an open pipe sparger and/or or drilled hole sparger.

In some embodiments, a bioreactor system includes a drilled hole sparger. In some embodiments, a drilled hole sparger has holes that are a size within a range of 0.05 mm to 5.0 mm. In some embodiments, a drilled hole sparger has 0.1 mm to 1.0 mm holes. In some embodiments, a drilled hole sparger has holes that are a size that is within a range bounded by a lower limit and an upper limit, the upper limit being larger than the lower limit. In some embodiments, the lower limit may be about 0.05 mm, about 0.06 mm, about 0.07 mm, about 0.08 mm, about 0.09 mm, about 0.1 mm, about 0.2 mm, about 0.3 mm, about 0.4 mm, about 0.5 mm, about 0.6 mm, about 0.7 mm, about 0.8 mm, about 0.9 mm, or about 1.0 mm. In some embodiments, the upper limit may be about 0.2 mm, about 0.3 mm, about 0.4 mm, about 0.5 mm, about 0.6 mm, about 0.7 mm, about 0.8 mm, about 0.9 mm, about 1.0 mm, about 1.25 mm, about 1.5 mm, about 1.75 mm, about 2.0 mm, about 2.25 mm, about 2.5 mm, about 2.75 mm, about 3.0 mm, about 3.5 mm, about 4.0 mm, about 4.5 mm, or about 5.0 mm.

In some embodiments, a bioreactor system includes a sintered sparger. In some embodiments, a bioreactor system includes a sparger that is located at the bottom of a bioreactor tank. In some embodiments, a bioreactor system includes a sparger that is located approximately centrally within a bioreactor tank.

In some embodiments, a bioreactor system includes a cell retention device. Cell retention devices suitable for use in bioreactor systems of the present disclosure include continuous centrifuges, alternating tangential flow filters (ATF), tangential flow membrane filters (TFF), dynamic filters, spin-filters, ultrasonic and dielectrophoretic separators, and gravity settlers. In some embodiments, a bioreactor system of the present disclosure includes a cell alternating tangential flow (ATF) device. In some embodiments, a bioreactor system includes a cell retention device that comprises one or more ATFs. In some embodiments, a bioreactor system includes a cell retention device that comprises two ATFs. In some embodiments, a bioreactor system includes a cell retention device that comprises three or more ATFs.

In some embodiments, a bioreactor system includes an impeller device. In some embodiments, an impeller is a bottom mounted within a bioreactor tank. In some embodiments, an impeller is located approximately centrally within a bioreactor tank. In some embodiments, a impeller device is magnetically driven. In some embodiments, a bioreactor system has an impeller agitation rate that delivers volumetric power input P/V of about 5 W/m$^3$ to about 500 W/m$^3$ Shear-Sensitive Cells In some instances, the methods, processes and systems of culturing of the present disclosure are for continuous culturing of shear-sensitive cells. The present disclosure encompasses the recognition that animal cells, having no cell wall, can be sensitive to fluid mechanical stresses of culturing in a stirred-tank bioreactor, such as, for example, agitation by the impeller and from the rising and bursting of bubbles, which are generated within the culture medium in the stirred tank to supply oxygen to the cells. If excessive, these fluid mechanical stresses can result in damage/death of animal cells. Moreover, the present disclosure encompasses a recognition that certain animal cells are more sensitive to shearing by mechanical stresses than others. For example, mouse myeloma cells can be more shear-sensitive than certain strains of CHO cells. The present disclosure provides methods, processes and systems are suitable for large-scale high density culturing of shear-sensitive cells.

Certain cells, e.g., animal cells, are known in the art to be sensitive to certain mechanical and/or aeration conditions during culturing (see, e.g., Gooch et al., *Curr. Opin. Biotech.* 4:193-196 (1993)). As used herein, a shear-sensitive cell is any animal cell that exhibits a level of sensitivity to shearing (e.g., that exhibit decreased cell viability) under conventional culture conditions (e.g., conventional large scale culture conditions). As discussed herein, in certain instances, when such shear-sensitive cells are cultured under conditions described herein, such cells exhibit an increased level of viability.

In some embodiments, a shear-sensitive cell is mammalian cell. In some embodiments, a shear-sensitive cell is a murine cell. In some embodiments, a shear-sensitive cell is from a mouse cell line. Murine (e.g., mouse) shear-sensitive cell lines include, for example, mouse myeloma cell lines. In some certain embodiments, shear-sensitive cells are selected from: NS0 cells and SP 2/0 cells.

In some embodiments, a shear-sensitive cell is human cell. Human shear-sensitive cell lines include, for example, HEK 293: human embryonic kidney 293; HT-1080: from a fibrosarcoma with an epithelial-like phenotype; PER.C6: from human embryonic retinal cells immortalized via transfection with the adenovirus E1 gene; CAP: from human amniocytes immortalized through an adenovirus type 5 E1 gene; HKB-11: created through polyethylene glycol fusion of HEK293-S and a human B-cell line; and HuH-7: from a human hepatocellular carcinoma. In some certain embodiments, shear-sensitive cells are selected from: HEK 293 cells, fibrosarcoma HT 1080 cells, PER.C6 cells, CAP cells, HKB-11 cells and HuH-7 cells.

In some certain embodiments, shear-sensitive cells for use in accordance with the present disclosure are SP 2/0 cells. In some embodiments, shear-sensitive cells for use in accordance with the present disclosure is engineered to include or express a cell product.

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

In some embodiments, a shear-sensitive cell that expresses a cell product as described herein is produced using recombinant methods. Recombinant expression of a gene, such as a gene encoding a polypeptide, such as an antibody agent described herein, can include construction of an expression vector containing a polynucleotide that encodes the polypeptide. Once a polynucleotide has been obtained, a vector for the production of the polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a shear-sensitive cell by conventional techniques, and transfected cells can then be cultured by methods as described herein to produce the cell product (e.g., a protein preparation, e.g., a recombinant protein, e.g., a glycoprotein, e.g., a fusion protein, e.g., an antibody agent).

Cells Culture Media

The present disclosure provides methods, processes, and systems for continuous cell culture (e.g., of shear-sensitive cells, e.g., a population of cells comprising shear-sensitive cells, e.g., a population of cells consisting of shear-sensitive cells) in a culture media sufficient for expression of a cell product. Cell culture media generally comprise an appropriate source of energy and compounds which regulate the cell cycle. Generally, culture media includes, for example amino acids, vitamins, inorganic salts, and glucose, which is known to those of skill in the art. In some embodiments, a cell culture media has a pH of 6 to 8. Media for animal cell culture are well established in the art, and are routinely optimized by the skilled artisan for the particular purpose and/or cell type.

In some embodiments, a cell culture media also includes an antifoam agent (e.g., antifoam C) within a range of 1 ppm to about 500 ppm. In some embodiments, shear-sensitive cells are cultured in a cell culture media that includes a shear-force protectant (e.g., Pluronic F-68). In some embodiments, shear-sensitive cells are cultured in a cell culture media that includes Pluronic F-68 at a concentration within a range of 1 g/L to 15 g/L. In some certain embodiments, a population of shear-sensitive cells can be cultured in a cell culture media that includes serum (e.g., fetal calf serum).

Cell Products

In some instances, a shear-sensitive cell or population of cells consisting of shear-sensitive cells is continuously cultured using a method, process, and/or of the present disclo-sure to express a cell product. In some embodiments, a cell product is or includes a nucleic acid, a lipid, a peptide, and/or a protein.

In some embodiments, a cell product is a recombinant protein. In some embodiments, a shear-sensitive cell of the present disclosure includes a nucleic acid that encodes a recombinant protein. In some embodiments, a cell product is a glycoprotein. In some embodiments, a recombinant protein is a fusion protein. In some embodiments, a shear-sensitive cell of the present disclosure includes a nucleic acid that encodes a fusion protein. In some embodiments, a recombinant protein is an Fc fusion protein. In some embodiments, a shear-sensitive cell of the present disclosure includes a nucleic acid that encodes an Fc fusion protein.

In some embodiments, a cell product is an antibody agent. In some embodiments, a shear-sensitive cell of the present disclosure includes a nucleic acid that encodes an antibody agent. In some embodiments, a cell product is a monoclonal antibody.

In some embodiments, a shear-sensitive cell of the present disclosure includes a nucleic acid that encodes a glycoprotein conjugate (e.g., Fc region or Fc fragment containing one or more N-glycosylation sites thereof that are conjugated or fused to one or more heterologous moieties). Heterologous moieties include, but are not limited to, peptides, polypeptides, proteins, fusion proteins, nucleic acid molecules, small molecules, mimetic agents, synthetic drugs, inorganic molecules, and organic molecules. In some instances, a glycoprotein conjugate is a fusion protein that comprises a peptide, polypeptide, protein scaffold, scFv, dsFv, diabody, Tandab, or an antibody mimetic fused to an Fc region, such as a glycosylated Fc region. A fusion protein can include a linker region connecting an Fc region to a heterologous moiety (see, e.g., Hallewell et al. (1989), J. Biol. Chem. 264, 5260-5268; Alfthan et al. (1995), Protein Eng. 8, 725-731; Robinson & Sauer (1996).)

In some embodiments, a shear-sensitive cell of the present disclosure includes a nucleic acid that encodes a protein that has been approved, e.g., under a secondary approval process, for therapeutic or diagnostic use in humans or animals.

In some embodiments, a shear-sensitive cell of the present disclosure includes a nucleic acid that encodes a protein that has the same primary amino acid sequence as a protein that has been approved, e.g., under a secondary approval process, for therapeutic or diagnostic use in humans or animals. In some embodiments, a shear-sensitive cell of the present disclosure includes a nucleic acid that encodes a protein that differs by no more than 1, 2, 3, 4, 5, 10, 15, 20, 25, or 30 residues with an approved therapeutic or diagnostic protein. In some embodiments, a shear-sensitive cell of the present disclosure includes a nucleic acid that encodes a protein that has at least 90, 95, 98, 99% or 100% sequence identity with that of an approved therapeutic or diagnostic protein. The terms the "same primary amino acid sequence", "a primary amino acid sequence that differs by no more than 1, 2, 3, 4, 5, 10, 15, 20, 25, or 30 residues", "sequences that have at least 98% or more sequence identity", or similar terms, relate to level of identity between primary amino acid sequences. In some embodiments, a protein preparation or product includes amino acid variants, e.g., species that differ at terminal residues, e.g., at one or two terminal residues. In some embodiments of such cases, sequence identity compared is the identity between the primary amino acid sequence of the most abundant (e.g., most abundant active) species in each of the products being compared. In some embodiments, sequence identity refers to the amino acid sequence encoded by a nucleic acid that can be used to make the product.

In some embodiments, a shear-sensitive cell of the present disclosure includes a nucleic acid that encodes a protein that has not been approved for therapeutic or diagnostic use in humans or animals.

Nonlimiting, exemplary recombinant proteins can include abatacept (Orencia®, Bristol-Myers Squibb), abciximab (ReoPro®, Roche), adalimumab (Humira®, Bristol-Myers Squibb), aflibercept (Eylea®, Regeneron Pharmaceuticals), alefacept (Amevive®, Astellas Pharma), alemtuzumab (Campath®, Genzyme/Bayer), basiliximab (Simulect®, Novartis), belatacept (Nulojix®, Bristol-Myers Squibb), belimumab (Benlysta®, GlaxoSmithKline), bevacizumab (Avastin®, Roche), canakinumab (Ilaris®, Novartis), brentuximab vedotin (Adcetris®, Seattle Genetics), certolizumab (CIMZIA®, UCB, Brussels, Belgium), cetuximab (Erbitux®, Merck-Serono), daclizumab (Zenapax®, Hoffmann-La Roche), denileukin diftitox (Ontak®, Eisai), denosumab (Prolia®, Amgen; Xgeva®, Amgen), eculizumab (Soliris®, Alexion Pharmaceuticals), efalizumab (Raptiva®, Genentech), etanercept (Enbrel®, Amgen-Pfizer), gemtuzumab (Mylotarg®, Pfizer), golimumab (Simponi®, Janssen), ibritumomab (Zevalin®, Spectrum Pharmaceuticals), infliximab (Remicade®, Centocor), ipilimumab (Yervoy™, Bristol-Myers Squibb), muromonab (Orthoclone OKT3®, Janssen-Cilag), natalizumab (Tysabri®, Biogen Idec, Elan), ofatumumab (Arzerra®, GlaxoSmithKline), omalizumab (Xolair®, Novartis), palivizumab (Synagis®, MedImmune), panitumumab (Vectibix®, Amgen), ranibizumab (Lucentis®, Genentech), rilonacept (Arcalyst®, Regeneron Pharmaceuticals), rituximab (MabThera®, Roche), tocilizumab (Actemra®, Genentech; RoActemra, Hoffman-La Roche) tositumomab (Bexxar®, GlaxoSmithKline), trastuzumab (Herceptin®, Roche), and ustekinumab (Stelara®, Janssen).

In some certain embodiments, a cell product is ustekinumab. In some embodiments, a shear-sensitive cell includes a nucleic acid that encodes ustekinumab.

In some embodiments, a shear-sensitive cell includes a nucleic acid that encodes an antibody agent that includes a heavy chain variable domain as set forth in SEQ ID NO.: 1 and a light chain variable domain as set forth in SEQ ID NO.: 2. In some embodiments, a shear-sensitive cell includes a nucleic acid that encodes an antibody agent that comprises a heavy chain comprising a sequence of SEQ ID NO.: 1 and a light chain comprising a sequence of SEQ ID NO.: 2. In some embodiments, a shear-sensitive cell includes a nucleic acid that encodes an antibody agent that includes HCDR1, HCDR2, and HCDR3 sequences as set forth in SEQ ID NO.: 1 and LCDR1, LCDR2, and LCDR3 sequences as set forth in SEQ ID NO.: 2.

SEQ ID NO.: 1—ustekinumab heavy chain sequence (bold indicates variable domain sequence with CDR sequences underlined)

EVQLVQSGAEVKKPGESLKISCKGSGYSFT<u>TYWLG</u>WVRQMPGKGLDWIG

IMSPVDSDIRYSPSFQGQVTMSVDKSITTAYLQWNSLKASDTAMYYCAR

RRPGQGYFDFWGQGTLVTVSSSSTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKRVEPKSCDKTHTCPPCPAPELLGGPSVFLF

-continued

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

SEQ ID NO.: 2—ustekinumab light chain sequence (bold indicates variable domain sequence with CDR sequences underlined)

DIQMTQSPSSLSASVGDRVTITC<u>RASQGISSWLA</u>WYQQKPEKAPKSLIY

<u>AASSLQS</u>GVPSRFSGSGSGTDFTLTISSLQPEDFATYYC<u>QQYNIYPYT</u>F

GQGTKLEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC

Pharmaceutical Compositions

A cell product (e.g., a recombinant protein, e.g., a glycoprotein, e.g., an antibody agent) produced or manufactured using any of the methods, systems and/or processes described herein can be incorporated into a pharmaceutical composition. Such a pharmaceutical composition may be useful in the prevention and/or treatment of diseases. Pharmaceutical compositions comprising a recombinant protein (e.g., a glycoprotein, e.g., an antibody agent) can be formulated by methods known to those skilled in the art (see, e.g., Remington's Pharmaceutical Sciences, 20th Ed., Lippincott Williams & Wilkins, 2000). The pharmaceutical composition can be administered parenterally in the form of an injectable formulation comprising a sterile solution or suspension in water or another pharmaceutically acceptable liquid. For example, the pharmaceutical composition can be formulated by suitably combining the cell product (e.g., a recombinant protein, e.g., a glycoprotein, e.g., an antibody agent) with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in a pharmaceutical preparation is such that a suitable dose within the designated range is provided.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the patient. A single dose of the pharmaceutical composition containing a cell product (e.g., a recombinant protein, e.g., a glycoprotein, e.g., an antibody agent) can be selected from a range of 0.001 mg/kg of body weight to 1000 mg/kg of body weight. In some embodiments, a dose can be selected in the range of 0.001 mg to 100,000 mg, but the present disclosure is not limited to such ranges. Dose and method of administration varies depending on the weight, age, condition, and the like of a patient in need thereof, and can be suitably selected as needed by those skilled in the art.

The disclosure is further illustrated by the following examples. The examples are provided for illustrative purposes only. They are not to be construed as limiting the scope or content of the disclosure in any way.

EXAMPLES

Example 1: Conventional Conditions for Continuous Culture of Shear-Sensitive Cells are Insufficient for Scaled Up Processes This example describes identification of a scale-up problem with continuous culturing of shear-sensitive cells. In particular, the present example describes the discovery that large-scale (e.g., 200 L) perfusion culturing of shear-sensitive cells without controlling gas exit velocity had impaired cell viability and insufficient viable cell concentrations for biological manufacture. Specifically, the present example describes scale up of perfusion culture methods of an exemplary shear-sensitive cell line, SP2/0, that has been engineered to include a nucleic acid encoding an exemplary cell product (e.g., an antibody agent, e.g., a monoclonal antibody).

Figure 2:
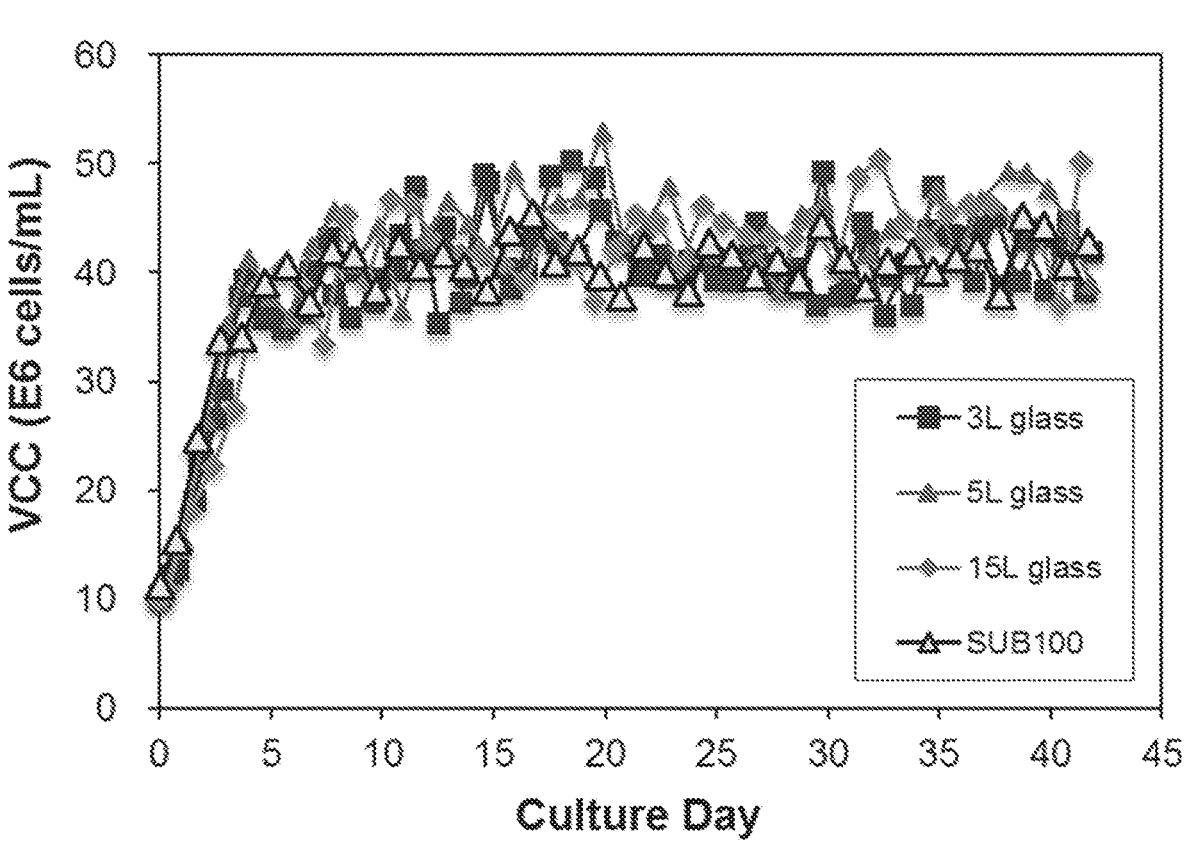
FIG. 2 depicts viable cell concentration (in 106 cells/mL) of exemplary shear-sensitive cells (e.g., SP2/0 cells) cultured by perfusion cultures at scales from 3 L to 100 L. Cells grown in 3 L (squares), 5 L (solid triangles), 15 L (diamonds) and 100 L (open triangles) cultures exhibited comparable cell growth and steady state viable cell concentrations.

Conventional conditions for continuous cell culture (e.g., perfusion cell culture) of exemplary shear-sensitive cells (e.g., SP2/0) expressing an exemplary antibody agent were assessed with small-scale continuous culture systems (e.g., at most 100 L), results are depicted in FIG. 2. Specifically, shear-sensitive cells grown in 3 L glass reactor, 5 L glass reactor, 15 L glass reactor and 100 L SUB 100 single use reactor systems exhibited comparable cell growth and steady state viable cell concentrations. Shear-sensitive cells cultured at 3 L, 5 L, 15 L and 100 L also had comparable productivity and product quality (data not shown).

Figure 3:
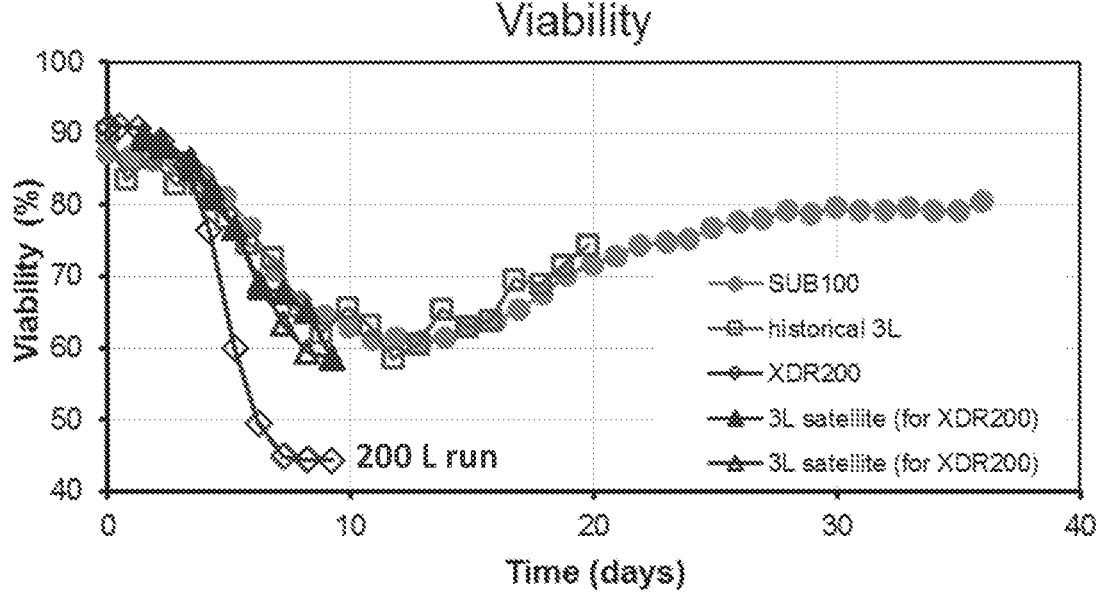
FIG. 3 depicts viable cell concentration (in 106 cells/mL) (top panel) and percent viability (bottom panel) of exemplary shear-sensitive cells (e.g., SP2/0 cells) cultured by perfusion cultures at scales from 3 L to 200 L. Solid circles represents 100 L culturing process, open squares represent historical 3 L control culture data, solid and open triangles represent additional 3 L culturing processes, and open diamons represents 200 L culturing process. Initial cell growth was observed in all samples, however, starting at day 4 the 200 L culture system exhibited both impaired cell growth and declining viable cell concentration.

Scale-up of continuous cell culture (e.g., perfusion cell culture) of exemplary shear-sensitive cells, SP2/0, to 200 L was attempted and results are depicted in FIG. 3. Specifically, the following exemplary stirred tank bioreactor systems were employed:

and provides methods of large-scale continuous cell culture (e.g., perfusion cell culture) that generate a high density of shear-sensitive cells (e.g., having a steady state viable cell concentration that is e.g., at least $20\times10^6$ cells/mL, e.g., at least $30\times10^6$ cells/mL, etc.).

In order to understand why cell growth and viability of shear-sensitive cells was impaired in 200 L continuous culture systems, a variety of parameters were analyzed. Protocols and conditions were reviewed to ensure there were no issues with raw materials (e.g., media, media prep filters, antifoam, inoculum, etc.). Parameters such as dissolved oxygen (DO), pH and temperature were consistent between the small-scale and large-scale cultures (data not shown).

Figure 4:
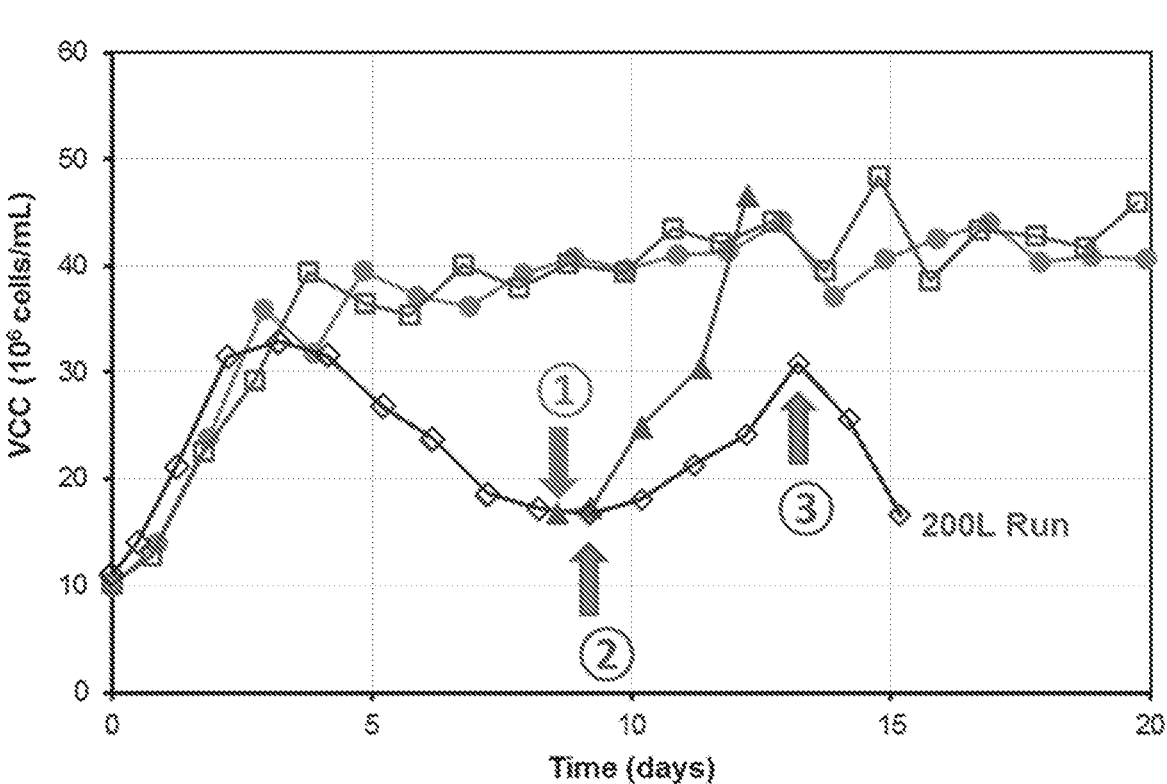
FIG. 4 depicts viable cell concentration (in 106 cells/mL) of exemplary shear-sensitive cells (e.g., SP2/0 cells) cultured by perfusion cultures at different scales and with varying gas exit velocities. Solid circles represents 100 L culturing process, open squares represent 3 L control cultures, open diamonds represents 200 L culturing process. At time point (1) 2 L of culture media from the 200 L culturing process is transferred to a 3 L culture, and this culture condition is represented by solid triangles. At time point (2) the control gas exit velocity of the 200 L culture is reduced to at most or equal to 10 m/s. At time point (3) the control gas exit velocity of the 200 L culture is again increased to a level at least 20 m/s.

Gas exit velocity (GEV) at a rate of >20 m/s was identified as a potential contributor to the impaired growth and viability. To assess this hypothesis, a portion of culture fluid (specifically, 2 L of cell culture fluid) was transferred from a 200 L bioreactor (XDR200 bioreactor) after 8 days of culturing to a benchtop 3 L bioreactor that has a maximum GEV of 3 m/s. The viable cell concentration of the remaining 200 L culturing system and the 3 L benchtop bioreactor was monitored. As shown in FIG. 4, viable cell concentration rapidly recovered in the 3 L benchtop bioreactor. Meanwhile, sparger gas exit velocity in the 200 L bioreactor was subsequently controlled (reduced) to a rate that is at most or equal to 10 m/s from culture day 9 to day 13. During this time, viability cell concentration recovered. Moreover, when GEV was then increased on day 13 to a level at least 20 m/s, the viable cell concentration rapidly decreased. These results suggest that GEV controlling at a level that is at most or equal to 10 m/s promotes cell viability for successful scale up (e.g., to pilot scale).

Continuous cell culture runs with 3 L perfusion bioreactors were performed with various gas exit velocities (GEVs) to determine a GEV threshold, which are depicted in FIG. 5. Specifically, and increase in GEV from 10 m/s to 16 m/s resulted in a rapid decreased in viable cell concentration. Similarly, maintaining a GEV at 13 m/s also resulted in an

|  | 200 L culture system<br>XDR200 (GE/Xcellerex) | 100 L culture system<br>SUB 100 (ThermoFisher/HyClone |
|---|---|---|
| Sparger | 2 × 5 × 1 mm holes<br>Up to 20 m/s gas exit velocity was<br>observed in XDR200 run at 9.5<br>slpm gas sparging rate | 570 × 0.18 mm holes<br>Up to 10 m/s gas exit velocity was<br>observed in SUB100 run at 8 slpm<br>gas sparging rate |
| Impeller | Magnetically-driven bottom mount<br>impeller; close to base of bioreactor<br>tank and directly above sparger | Located in the middle of the culture<br>tank |

While initial growth was observed in all samples, however, as depicted in FIG. 3, starting at day 4 the 200 L culture process utilizing GE/Xcellerex XDR200 disposable reactor system exhibited both impaired cell growth (viable cell concentration (in $10^6$ cells/mL) (top)) and declining viability of shear-sensitive cells (percent viability (bottom)). Thus the present example demonstrates that improved methods are needed in order to successfully continuously culture shear-sensitive cells at a large scale (e.g., at least 200 L).

Example 2: Root Cause Analysis for Scaled Continuous Cell Culture of Shear-Sensitive Cells The present example identified the source of impaired cell growth and viability of shear-sensitive cells, SP2/0 cells, at large-scale (e.g., 200 L or greater) described in Example 1 eventual crash in viable cell concentration after 12 days of culture. Meanwhile, decreasing GEV from 16 m/s to 10 m/s increased viable cell concentration.

Thus, the present example demonstrates that by controlling sparger gas exit velocity below 20 m/s (e.g., below 10 m/s), continuous culturing of shear-sensitive cells can be successfully scaled up to a large-scale culture (e.g., 200 L or greater, e.g., 250 L or greater) and produce a high density of shear-sensitive cells (e.g., with a steady state concentration that is e.g., at least $20\times10^6$ cells/mL, e.g., at least $30\times10^6$ cells/mL).

The effect of dissolved CO2 on cell culture viability of shear-sensitive cells was also assessed and the results are shown in FIG. 6. Specifically, the exemplary shear-sensitive cells (SP2/0 cells) were found to be sensitive to dissolve carbon dioxide ($pCO_2$). A negative impact on cell culture performance was found when $pCO_2$ was $\geq$90 mmHg.

23

This example demonstrates that cell growth and viability of shear-sensitive cells of large-scale continuous cultures can be restored by controlling gas exit velocity (e.g., at a below 10 m/s). Moreover, this example also shows that controlling $pCO_2$ levels also is beneficial for large-scale culturing of shear-sensitive cells at a high density.

Example 3: Large-Scale Continuous Cell Culture of Shear-Sensitive Cells

The present example describes successful large-scale continuous culture of shear-sensitive cells applying the understanding of Examples 1 and 2. Specifically, continuous cell culture run a 250 L perfusion reactor (SUB250) was performed with both GEV and $pCO_2$ controlled. FIG. 7A and FIG. 7B provide cell density and cell viability comparison among 3 L, 5 L, 15 L, 100 L (SUB100) and 250 L (SUB250). Specifically, FIG. 7A and FIG. 7B provide additional analysis of cell viability at different cell culture scales (e.g. 100 L, e.g., 250 L) with GEV and $pCO_2$ controlled at different levels. A SUB100, 100 L bioreactor includes 570×0.18 mm holes and a SUB250, 250 L bioreactor includes 760×0.233 mm holes. As shown in FIG. 7A, continuous cell cultures at a 250 L scale (SUB250) with a GEV controlled at about 7 m/s and a dissolved carbon dioxide of at most 80 mmHg exhibited similar cell viability as small-scale cultures. FIG. 8 provides a summary of predictive models for 250 L cultures (e.g., using a SUB250 bioreactor system) for different parameters. Notably, using these models for dissolved CO2 at 100 L and 250 L, the predicted levels of CO2 was highly similar to the data actually obtained (not shown).

FIG. 9 shows that these continuous cultures of shear-sensitive cells at 3 L, 100 L, and 250 L, all show comparable total glycan levels (top panel) and comparable sialic acid content (bottom panel). Thus, the present example demonstrates successful scale up of high cell density shear-sensitive cells (SP2/0) with a perfusion culture process to a 250 L scale (e.g., with a Thermo Fisher/HyClone SUB250 (250L) stirred tank bioreactor) (FIG. 7A, FIG. 7B, and FIG. 9).

Thus, the present example also demonstrates that controlling $pCO_2$ levels also is beneficial for large-scale culturing (e.g., at least 100 L, e.g., 250 L) of shear-sensitive cells at a high density (e.g., with a steady state concentration that is e.g., at least $20\times10^6$ cells/mL, e.g., at least $30\times10^6$ cells/mL). By controlling $pCO_2$ below 80 mmHg and sparger gas exit velocity below 10 m/s, we were able to successfully scale up our process from 3 L to 250 L stirred tank bioreactor.

Thus the present example supports controlling GEV from a sparger at a rate <10 m/s while maintaining $pCO_2 \leq 80$ mmHg for successful scale up of perfusion cultures of shear-sensitive cells.

Example 4: Scaling Continuous Cell Culture to Production Scale

Figure 10:
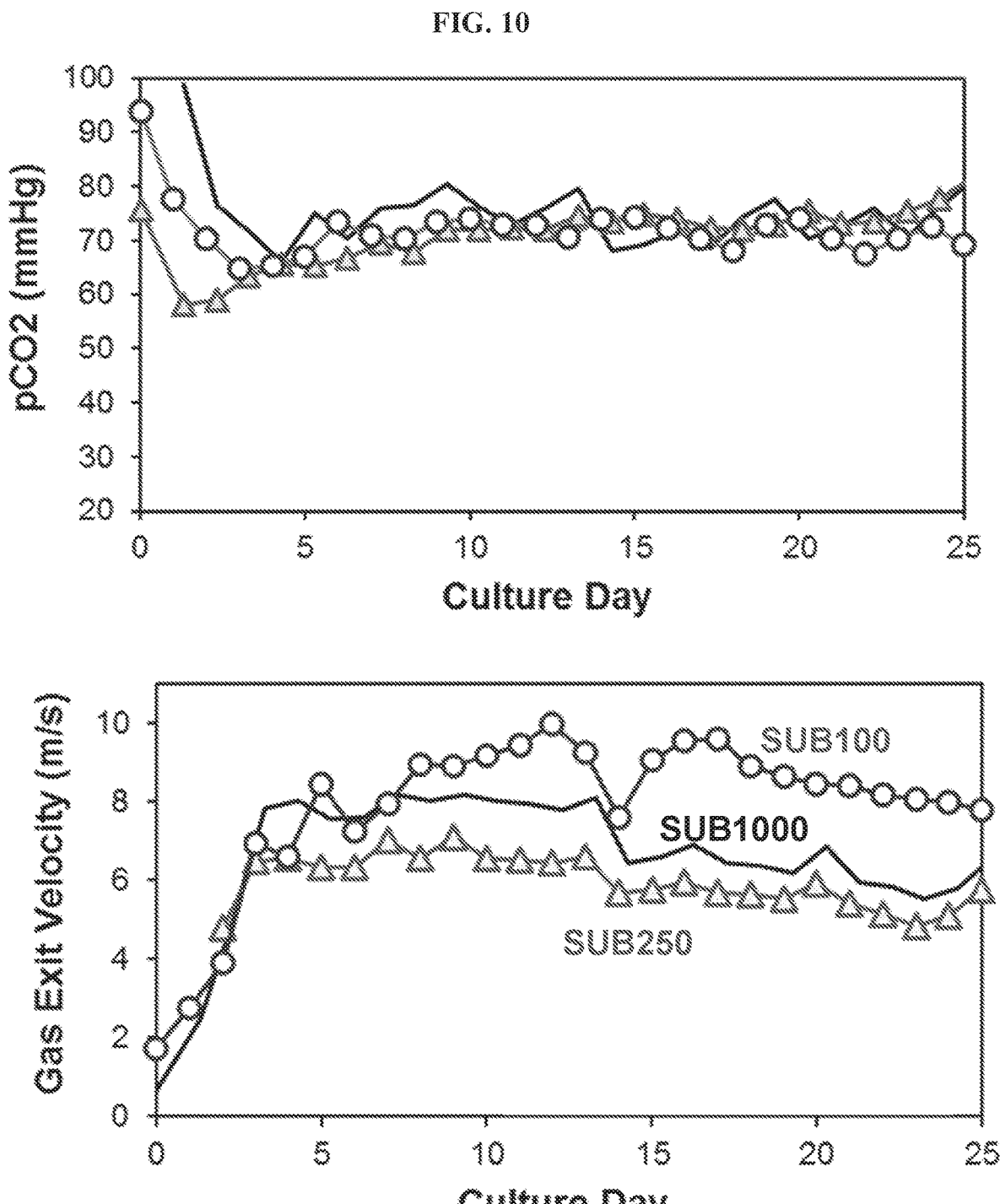
FIG. 10 depicts predicted dissolved $CO_2$ (top panel) and gas exit velocity (bottom panel) for 1000 L continuous cultures of shear-sensitive cells (solid black lines) relative to demonstrated 250 L (represented by triangles) and 100 L (represented by circles) culture processes.

This example describes modeling different parameters for large-scale continuous culturing of shear-sensitive cells at production scale (e.g., 1000 L or greater). As shown in FIG. 10, predicted parameters for dissolved CO2 (top panel) and gas exit velocity (bottom panel) for 1000 L continuous cultures of shear-sensitive cells are comparable to the levels demonstrated in 250 L and 100 L culture processes. Moreover, FIG. 11 provides a table summarizing predicted models for 1000 L cultures (e.g., using a SUB 1000 bioreactor system) for different parameters. Thus, the parameters determined for large-scale (e.g., pilot scale) are expected to apply for even larger cultures, such as those with 1000 L bioreactor systems.

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for culturing a population of shear-sensitive cells comprising:

culturing a population of cells consisting of shear-sensitive cells in a perfusion bioreactor system with at least 100 L of culture media, wherein the culture media has a level of dissolved carbon dioxide that is at most 80 mmHg, and a gas exit velocity that is 10 m/s or less to achieve a steady state viable cell concentration in the culture media within a range of $20 \times 10^6$ cells/mL to $15 \times 10^7$ cells/mL, wherein the shear-sensitive cells are HEK 293 cells, fibrosarcoma HT 1080 cells, PER.C6 cells, CAP cells, HKB-11 cells, HuH-7 cells, NS0 cells, or SP 2/0 cells.

2. The method of claim 1, wherein the gas exit velocity is controlled at least until the bioreactor system reaches the steady state condition.

3. The method of claim 2, wherein the steady state condition includes having a viable cell concentration that varies at most 20% over a period of 5 days.

4. The method of claim 1, wherein the gas exit velocity is controlled throughout the culturing step.

5. The method of claim 1, wherein the culturing the population of cells consisting of shear-sensitive cells in the perfusion bioreactor system to achieve the steady state viable cell concentration further comprises bleeding or removing excess cells and/or non-viable cells.

6. The method of claim 1, wherein the bioreactor system includes at least 200 L, at least 500 L, at least 1,000 L, or at least 2,000 L of culture media.

7. The method of claim 1, wherein culturing is performed for a duration of 30 to 60 days.

8. The method of claim 1, wherein the method further comprises measuring the viable cell concentration.

9. The method of claim 8, wherein the measured viable cell concentration is within a range of $30 \times 10^6$ cells/mL to $15 \times 10^7$ cells/mL, $40 \times 10^6$ cells/mL to $15 \times 10^7$ cells/mL, or $50 \times 10^6$ cells/mL to $15 \times 10^7$ cells/mL.

10. The method of claim 1, wherein the shear-sensitive cells are human cells or murine cells.

11. The method of claim 1, wherein the bioreactor system includes a cell retention device, wherein the cell retention device is or includes a continuous centrifuge, an alternating tangential flow filter (ATF), a tangential flow membrane filter (TFF), a dynamic filter, a spin-filter, an ultrasonic and dielectrophoretic separator, and/or a gravity settler.

12. The method of claim 1, wherein the bioreactor system comprises a stirred tank bioreactor tank, wherein the bioreactor tank has a capacity of at least 100 L, at least 200 L, at least 500 L, at least 1,000 L, or at least 2,000 L.

13. The method of claim 1, wherein the bioreactor system includes a sparger.

14. The method of claim 13, wherein the sparger is a drilled hole sparger or an open pipe sparger.

15. The method of claim 1, wherein the culturing the population of cells is performed under conditions to express a cell product that comprises one or more of a nucleic acid, a lipid, a peptide, and a protein.

16. The method of claim 15, wherein the cell product is an antibody agent.

17. The method of claim 15, wherein the method further comprises isolating the cell product from at least a portion of the shear-sensitive cells and/or isolating the cell product from at least a portion of the culture media.

18. A continuous culture process for culturing a population of cells consisting of shear-sensitive cells, comprising:

controlling gas exit velocity of a bioreactor system so that the gas exit velocity does not exceed a rate of 10 m/s, wherein the bioreactor system comprises at least 100 L of culture media, wherein the culture media has a level of dissolved carbon dioxide that is at most 80 mmHg, and wherein the population of cells achieves a steady state viable cell concentration within a range of $20 \times 10^6$ cells/mL to $15 \times 10^7$ cells/mL, wherein the shear-sensitive cells are HEK 293 cells, fibrosarcoma HT 1080 cells, PER.C6 cells, CAP cells, HKB-11 cells, Hull-7 cells, NS0 cells, or SP 2/0 cells.

19. The method of claim 14, wherein the drilled hole sparger comprises holes having a diameter of about 0.2 mm to about 0.3 mm.

* * * * *

SEQUENCE LISTING

<160> NUMBER OF SEQ ID NOS: 2

<210> SEQ ID NO 1
<211> LENGTH: 449
<212> TYPE: PRT
<213> ORGANISM: Homo sapiens

<400> SEQUENCE: 1

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly

-continued

```
                100                 105                 110
Thr Leu Val Thr Val Ser Ser Ser Ser Thr Lys Gly Pro Ser Val Phe
            115                 120                 125
Pro Leu Ala Pro Ser Ser Lys Ser Thr Ser Gly Gly Thr Ala Ala Leu
        130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

```
<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
```

-continued

```
        20                25                30

Leu Ala Trp Tyr Gln Gln Lys Pro Glu Lys Ala Pro Lys Ser Leu Ile
        35                40                45

Tyr Ala Ala Ser Ser Leu Gln Ser Gly Val Pro Ser Arg Phe Ser Gly
    50                55                60

Ser Gly Ser Gly Thr Asp Phe Thr Leu Thr Ile Ser Ser Leu Gln Pro
65                70                75                80

Glu Asp Phe Ala Thr Tyr Tyr Cys Gln Gln Tyr Asn Ile Tyr Pro Tyr
                85                90                95

Thr Phe Gly Gln Gly Thr Lys Leu Glu Ile Lys Arg Thr Val Ala Ala
                100               105               110

Pro Ser Val Phe Ile Phe Pro Pro Ser Asp Glu Gln Leu Lys Ser Gly
        115               120               125

Thr Ala Ser Val Val Cys Leu Leu Asn Asn Phe Tyr Pro Arg Glu Ala
    130               135               140

Lys Val Gln Trp Lys Val Asp Asn Ala Leu Gln Ser Gly Asn Ser Gln
145               150               155               160

Glu Ser Val Thr Glu Gln Asp Ser Lys Asp Ser Thr Tyr Ser Leu Ser
            165               170               175

Ser Thr Leu Thr Leu Ser Lys Ala Asp Tyr Glu Lys His Lys Val Tyr
            180               185               190

Ala Cys Glu Val Thr His Gln Gly Leu Ser Ser Pro Val Thr Lys Ser
    195               200               205

Phe Asn Arg Gly Glu Cys
    210
```